(12) United States Patent
Anderson et al.

(10) Patent No.: US 9,456,861 B2
(45) Date of Patent: Oct. 4, 2016

(54) DISPENSING ASSEMBLY HAVING MIXING AND PLUNGING ASSEMBLY, AND RELATED METHODS

(71) Applicant: Nordson Corporation, Westlake, OH (US)

(72) Inventors: Benjamin B. Anderson, Wheeling, IL (US); Kevin C. Geppert, Eagan, MN (US); Jon E. Hoogenakker, Inver Grove Heights, MN (US); Huadong Lou, Plymouth, MN (US); Zachary Rzeszutek, Minneapolis, MN (US); Mark Stevenson, Cottage Grove, MN (US)

(73) Assignee: Nordson Corporation, Westlake, OH (US)

( * ) Notice: Subject to any disclaimer, the term of this patent is extended or adjusted under 35 U.S.C. 154(b) by 170 days.

(21) Appl. No.: 14/311,945

(22) Filed: Jun. 23, 2014

(65) Prior Publication Data
US 2014/0378937 A1 Dec. 25, 2014

Related U.S. Application Data

(60) Provisional application No. 61/838,588, filed on Jun. 24, 2013.

(51) Int. Cl.
*A61B 19/00* (2006.01)
*A61B 17/88* (2006.01)
(Continued)

(52) U.S. Cl.
CPC ....... *A61B 17/8822* (2013.01); *B01F 11/0054* (2013.01); *B01F 13/0023* (2013.01); *B01F 15/00051* (2013.01); *B01F 15/0279* (2013.01); *A61B 2017/8838* (2013.01); *B01F 2215/0029* (2013.01)

(58) Field of Classification Search
CPC .................. A61B 17/8822; A61B 2017/8838; B01F 11/0054; B01F 13/0023; B01F 15/00051
USPC ....................................... 604/92, 82
See application file for complete search history.

(56) References Cited

U.S. PATENT DOCUMENTS 7,879,002 B2 * 2/2011 Jessop .................... A61C 5/068
366/255
8,061,887 B2 11/2011 Henniges et al.
(Continued)

FOREIGN PATENT DOCUMENTS

GB 2338428 A 12/1999
WO 9949818 A1 10/1999
(Continued)

OTHER PUBLICATIONS

European Patent Office, International Search Report and Written Opinion in PCT Application Serial No. PCT/US2014/043774, Oct. 8, 2014.

*Primary Examiner* — Leslie Deak
(74) *Attorney, Agent, or Firm* — Baker & Hostetler LLP

(57) ABSTRACT

A dispensing assembly includes a syringe body having a barrel and a dispensing tip. The dispensing assembly further includes a mixing and plunging assembly configured for coupling with the syringe body and comprising a mixer and a plunger. The mixer is configured for mixing material in the barrel and has a rod and a mixing element removably connected with the rod. The plunger is configured to dispense material from the barrel through the dispensing tip. Also, the rod is configured to be detached from the mixing element and used to push material out of the dispensing tip.

21 Claims, 23 Drawing Sheets

(51) Int. Cl.
 *B01F 11/00* (2006.01)
 *B01F 13/00* (2006.01)
 *B01F 15/00* (2006.01)
 *B01F 15/02* (2006.01)

(56) References Cited

U.S. PATENT DOCUMENTS

2005/0105385 A1 5/2005 McGill et al.

2008/0304355 A1* 12/2008 Sattig ................ A61B 17/8825
  366/133
2012/0330229 A1 12/2012 Greter

FOREIGN PATENT DOCUMENTS

| WO | 2007008721 A1 | 1/2007 |
| WO | 2008153513 A2 | 12/2008 |
| WO | 2009105905 A1 | 9/2009 |
| WO | 2012066905 A1 | 5/2012 |
| WO | 2012174670 A1 | 12/2012 |

* cited by examiner

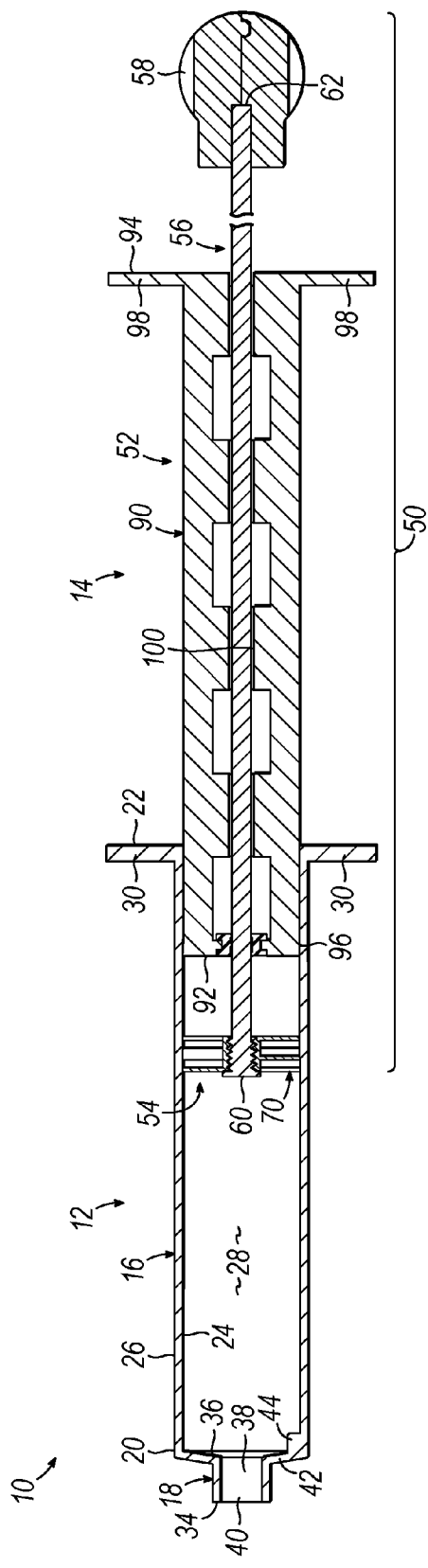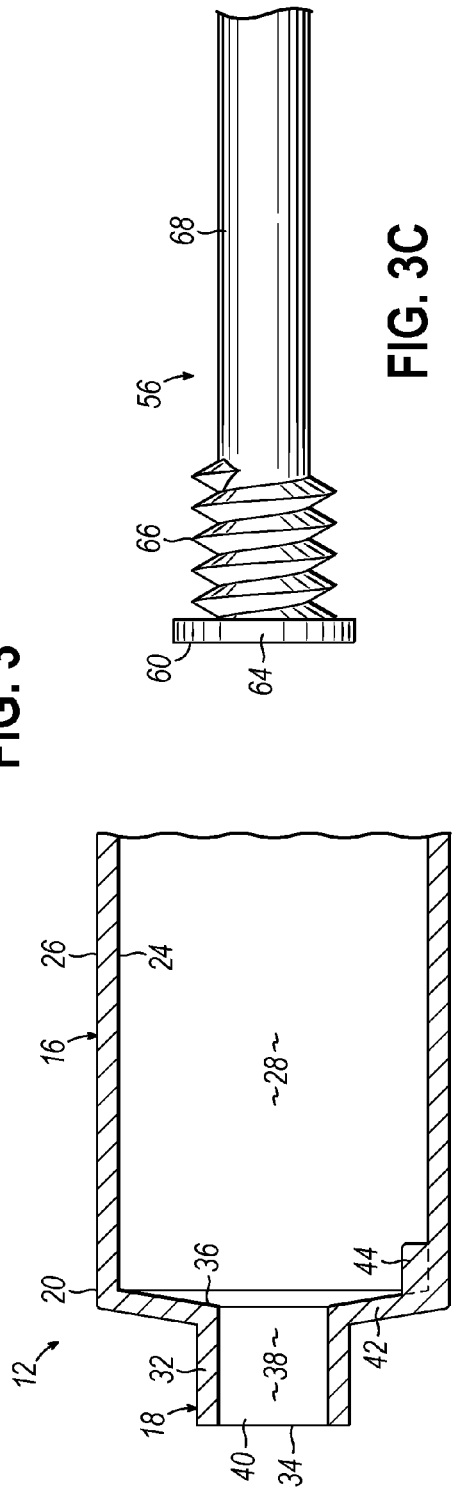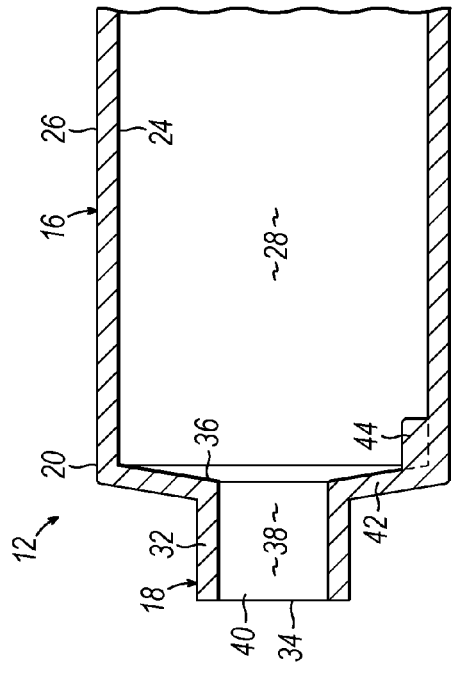

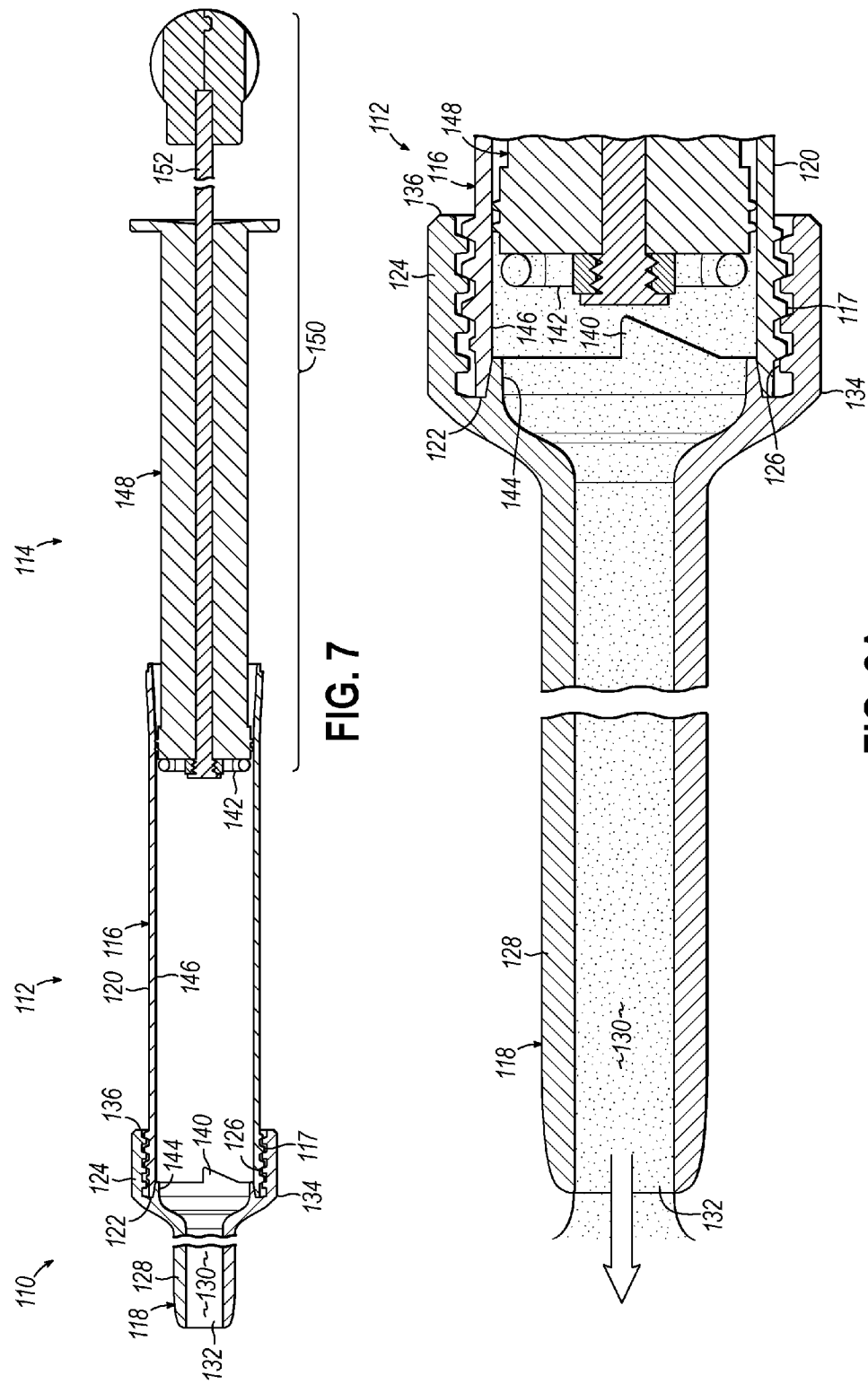

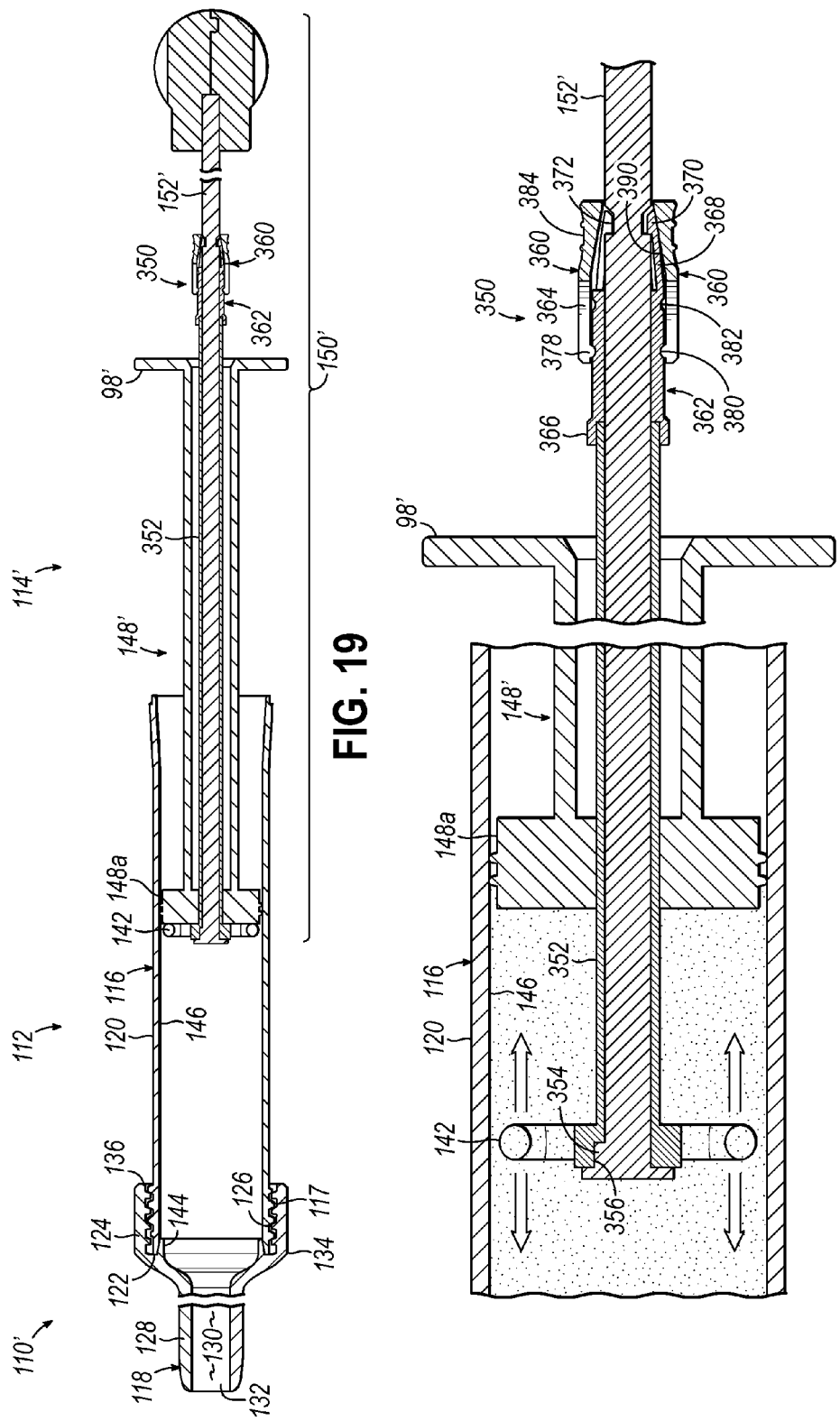

DISPENSING ASSEMBLY HAVING MIXING AND PLUNGING ASSEMBLY, AND RELATED METHODS

CROSS-REFERENCE TO RELATED APPLICATION

This application claims the benefit of application Ser. No. 61/838,588 filed Jun. 24, 2013, the disclosure of which is hereby incorporated by reference herein.

FIELD OF THE INVENTION

The present invention generally relates to dispensing equipment, and more particularly to devices used for dispensing materials such as bone graft materials.

BACKGROUND

Biomaterials are sometimes used in medical applications. For example, bone grafting is a surgical procedure for repairing bones and typically involves introducing a bone graft material (which is a type of biomaterial) into an area of bone that requires repair, such as a fracture. The bone graft material is intended to stimulate growth of healthy native bone tissue, and new native bone tissue may eventually replace the bone graft material completely. Bone graft material typically includes a combination of crushed bone and a liquid component, such as blood, plasma, or growth factors. Bone graft materials can be allograft (derived from a human other than the one receiving the graft), autograft (derived from the human receiving the graft), and synthetic (created from, for example, ceramics like calcium phosphates).

Bone graft materials are typically delivered to a surgical site using syringe-like delivery devices, which often include small-diameter dispensing tips, such as cannulus devices. In addition, the components of the bone graft material are sometimes brought together and combined to form the bone graft material in the delivery device. The bone graft material is then dispensed from the delivery device. This often involves using a syringe plunger to advance an amount of bone graft material from a syringe barrel and through a dispensing tip, and then dispensing the bone graft material from the dispensing tip at the surgical site. The dispensing tip may be integrally formed with or removable from the syringe barrel, and may have various lengths.

Once the syringe plunger is completely depressed in the syringe barrel, all or nearly all of the bone graft material is expelled from the syringe barrel. However, the dispensing tip still contains an amount of bone graft material, and further operation of the syringe plunger is ineffective for advancing that bone graft material out of the dispensing tip. This prevents the bone graft material that is trapped in the dispensing tip from being used during the surgical procedure, and leads to wasting an amount of the bone graft material. Wasting bone graft material is undesirable, however, as its components are costly. In addition, this drawback to current devices requires that more bone graft material be prepared than is actually required at the surgical site, in order to offset the amount that is trapped in the dispensing tip.

SUMMARY

According to one embodiment of the invention, a dispensing assembly includes a syringe body having a barrel and a dispensing tip. The dispensing assembly further includes a mixing and plunging assembly configured for coupling with the syringe body and comprising a mixer and a plunger. The mixer is configured for mixing material in the barrel and has a rod and a mixing element removably connected with the rod. The plunger is configured to dispense material from the barrel through the dispensing tip. Also, the rod is configured to be detached from the mixing element and used to push material out of the dispensing tip.

According to another embodiment of the invention, a method of dispensing material using a dispensing assembly is provided. The dispensing assembly includes a syringe body and a mixing and plunging assembly. The method includes moving a plunger of the mixing and plunging assembly to advance material from a barrel of the syringe body through a dispensing tip of the syringe body and out a dispensing tip opening of the syringe body. The method further includes detaching a mixing element from a rod of the mixing and plunging assembly, and moving the rod into the dispensing tip to advance material in the dispensing tip out of the dispensing tip opening.

According to another embodiment of the invention, a dispensing assembly includes a syringe body having a barrel and a dispensing tip. The dispensing assembly further includes a plunging assembly configured for coupling with the syringe body and including a plunger and a rod. The plunger is configured to dispense material from the barrel through the dispensing tip. The rod is configured to be moved relative to the plunger and the syringe body into the dispensing tip to push material out of the dispensing tip.

Various additional features and advantages of the invention will become more apparent to those of ordinary skill in the art upon review of the following detailed description of the illustrative embodiments taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

FIG. 3 is a cross-sectional view taken along line 3-3 in FIG. 1.

FIGS. 3A and 3B are detailed views showing portions of FIG. 3.

FIG. 3C is a plan view showing a rod of a mixing and plunging assembly.

FIG. 7 is a cross-sectional view taken along line 7-7 in FIG. 5.

FIGS. 8A-8B are cross-sectional detailed views showing operational steps of using the dispensing assembly of FIG. 5 to dispense a bone graft material.

FIG. 19 is a cross sectional view taken along line 19-19 of FIG. 16.

FIG. 20 is an enlarged cross sectional view, similar to FIG. 19, but illustrating the mixing operation being performed within the syringe body.

DETAILED DESCRIPTION

Figure 1:
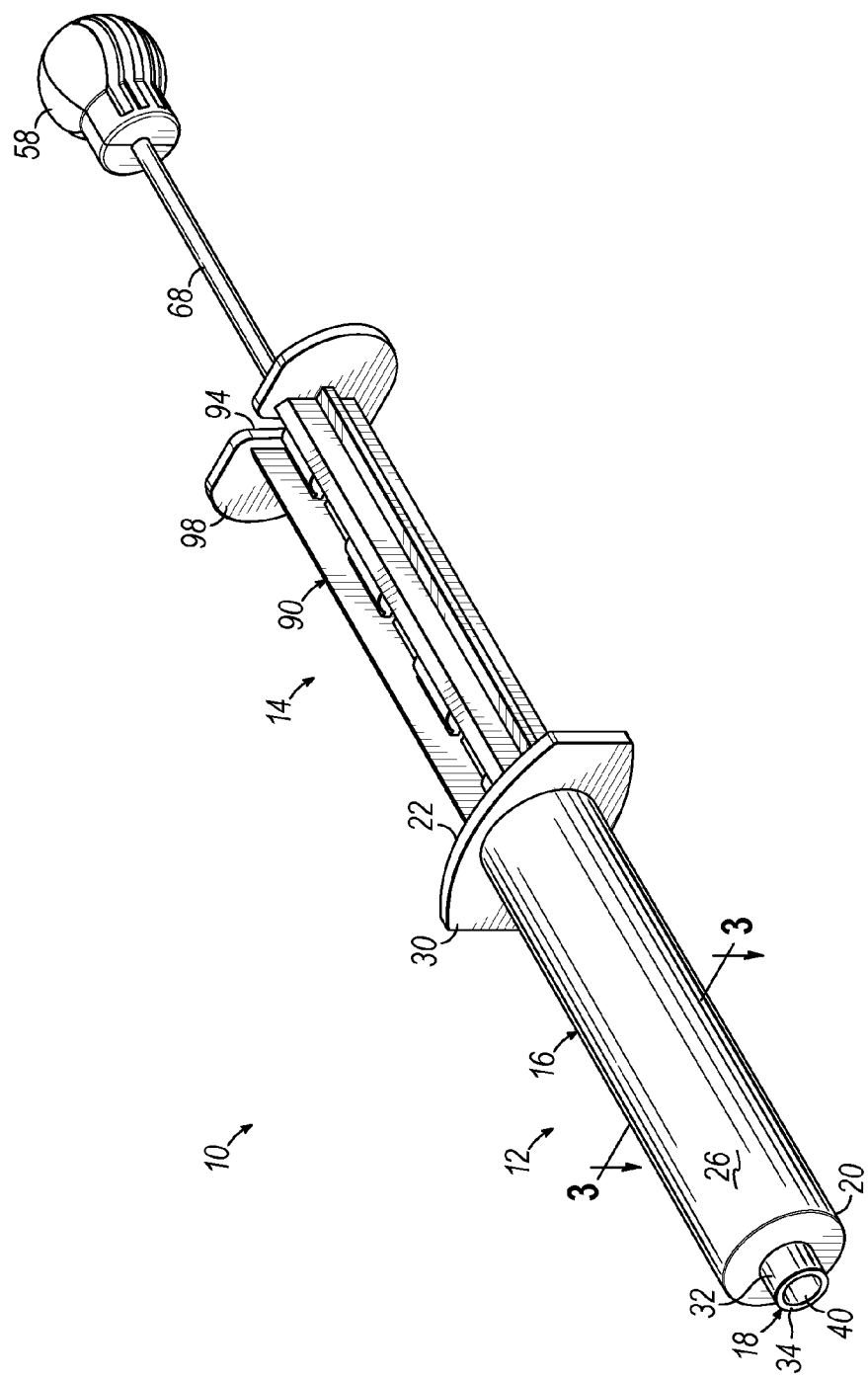
FIG. 1 is an isometric view showing a dispensing assembly constructed according to an embodiment of the present invention.

Referring to the figures, and beginning with FIG. 1, an exemplary dispensing assembly 10 is shown and includes a syringe body 12 and a mixing and plunging assembly 14. As will be apparent from the following discussion, the dispensing assembly 10 is useful for dispensing material, and for mixing material components in the syringe body 12 to form the material. In addition, the mixing and plunging assembly 14 includes features for increasing the amount of material that can be dispensed from the syringe body 12. This reduces the amount of material that would otherwise be left behind in the syringe body 12. In the embodiments shown and described below, the material that is dispensed is a bone graft material, such as what is used in a bone grafting procedure.

Referring to FIGS. 1, 2, 3, and 3A, the syringe body 12 includes a barrel 16 and a dispensing tip 18. The barrel 16 extends between a distal, or first, end 20 and an proximal, or second, end 22. The barrel 16 has a generally tubular shape and includes an interior surface 24 and an exterior surface 26. A passageway 28 extends in the barrel 16 between the ends 20, 22, and is generally defined within the interior surface 24. The passageway 28 is configured to hold bone graft material that is to be dispensed by the dispensing assembly 10. Finger tabs 30 can be provided near the proximal end 22 of the barrel 16 for a user to grasp, for example.

The dispensing tip 18 is positioned generally near the distal end 20 of the barrel 16 and includes a dispensing tube 32 having a reduced diameter as compared with the barrel 16. The dispensing tip 18 may also be referred to as a cannulus or cannulus device, and can have any suitable length. The dispensing tube 32 generally extends between a distal, or first, end 34 and an proximal, or second, end 36. A dispensing passageway 38 extends in the dispensing tube 32 and opens at a dispensing opening 40 at the distal end 34 thereof. The passageway 28 of the barrel 16 communicates with the passageway 38 of the dispensing tube 32 so that bone graft material contained within the passageway 28 of the barrel 16 can be advanced into the passageway 38 of the dispensing tube 32. Bone graft material is discharged or dispensed from the dispensing assembly 10 through the dispensing opening 40. A barrel closure 42 is positioned generally near the distal end 20 of the barrel 16 and connects the barrel 16 with the dispensing tip 18. In particular, the barrel closure 42 is generally annular shaped and extends from the barrel 16 to the dispensing tube 32, near the proximal end 36 of the tube 32. In the embodiment shown, the barrel 16 and the dispensing tip 18 are generally integrally formed with each other, and with the barrel closure 42.

Figure 3B:
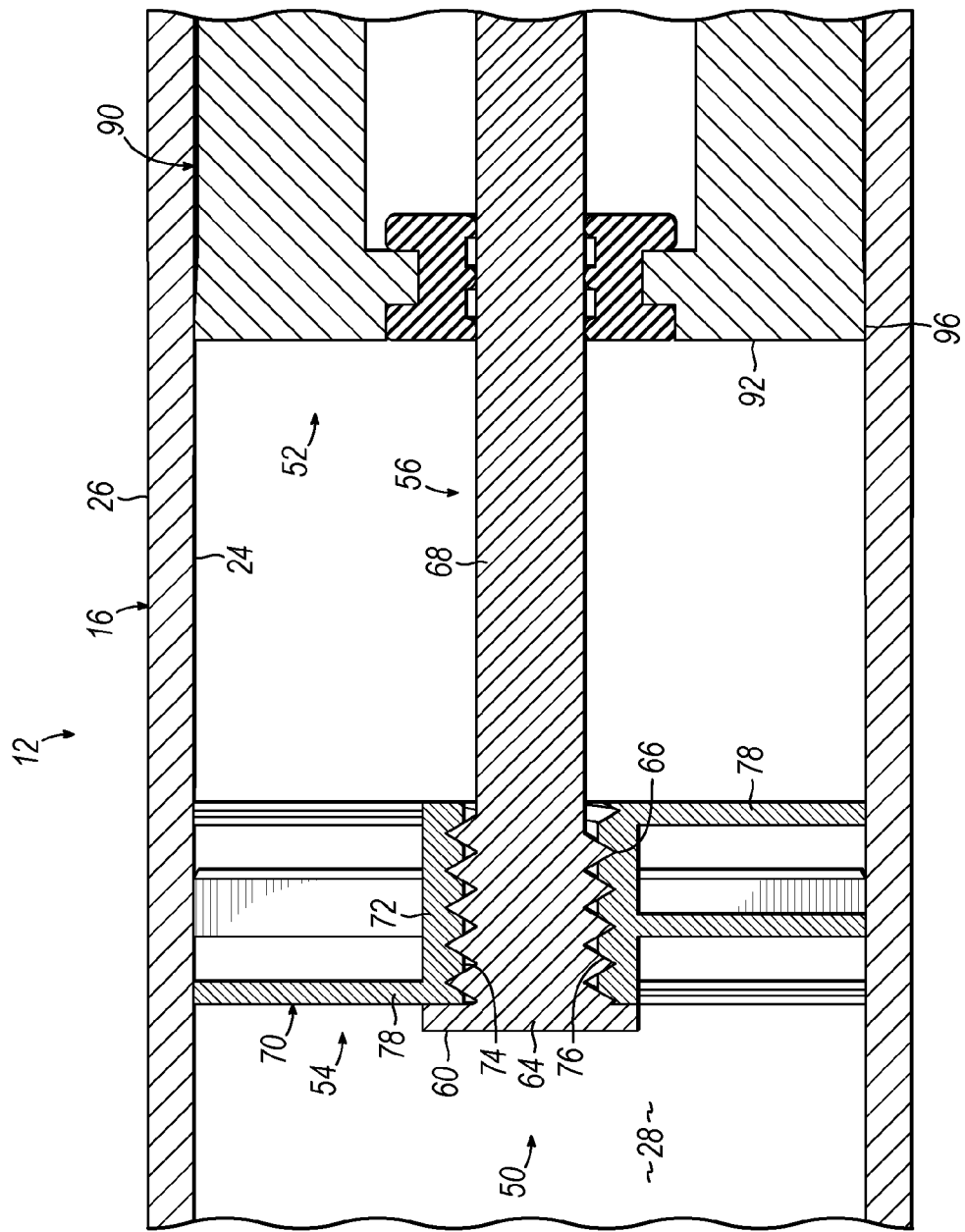
Figure 4A:
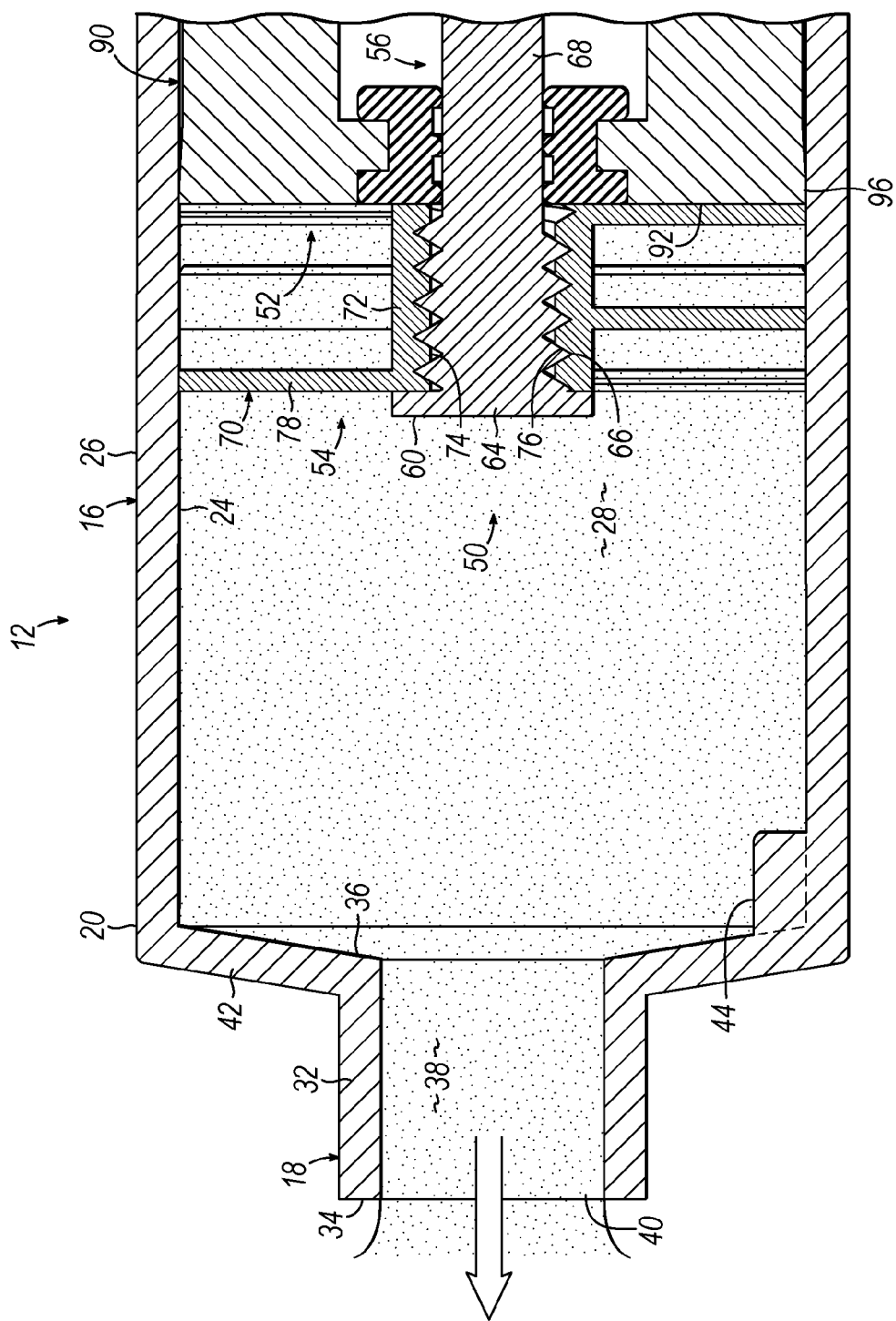
FIGS. 4A-4C are cross-sectional detailed views showing operational steps of using the dispensing assembly of FIG. 1 to dispense a bone graft material.
Figure 4B:
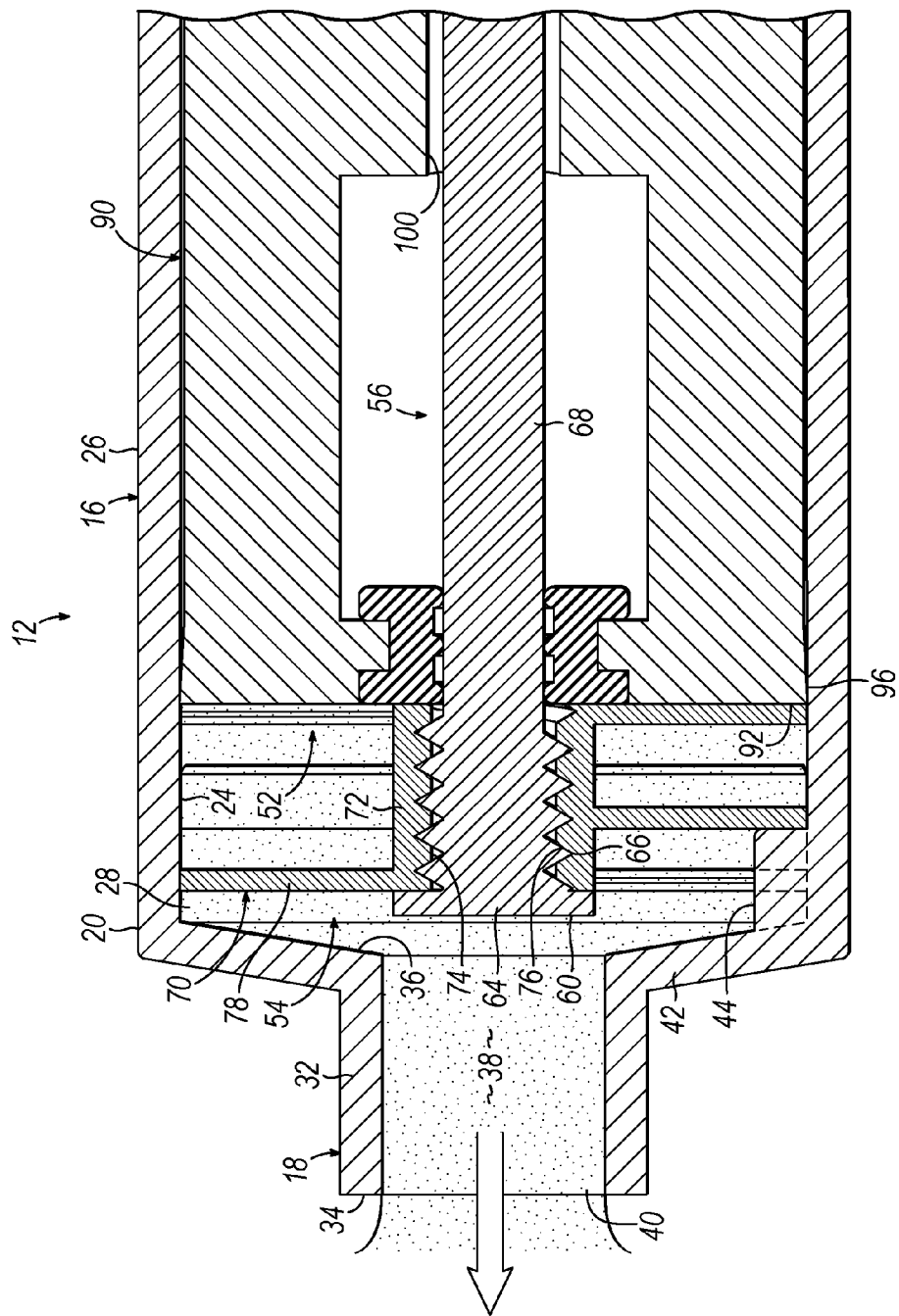
Figure 4C:
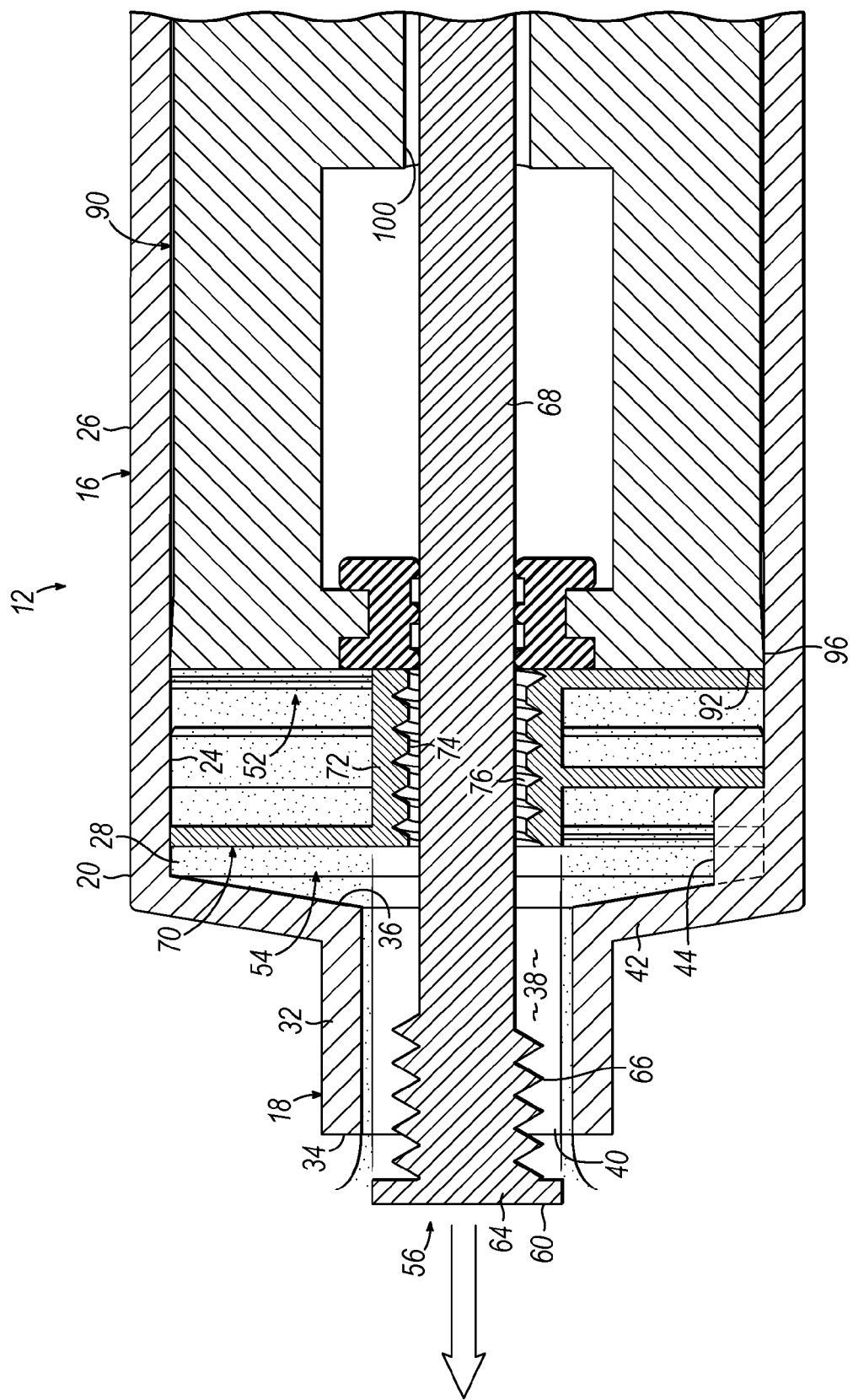
Figure 5:
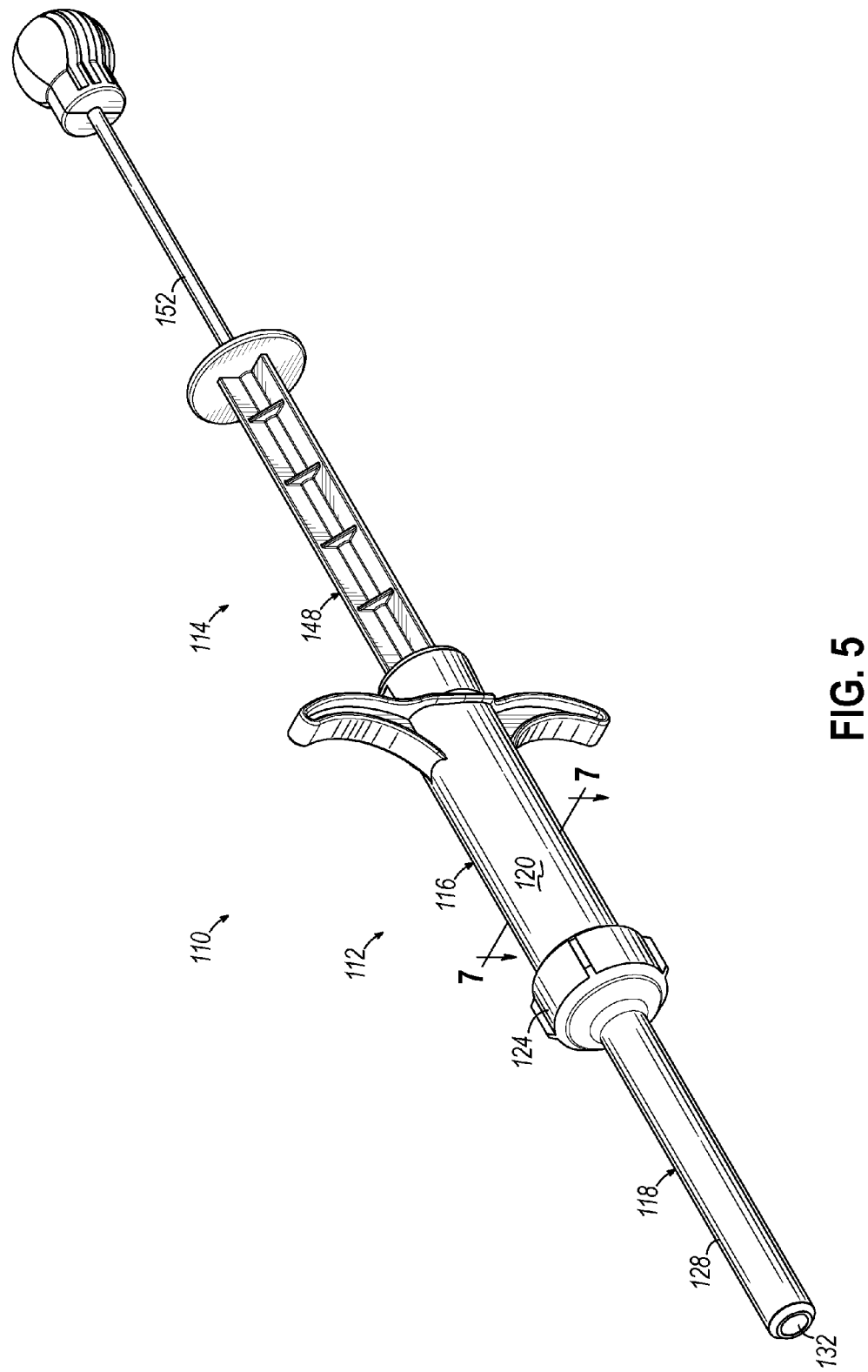
FIG. 5 is an isometric view showing a dispensing assembly constructed according to another embodiment of the present invention.
Figure 6:
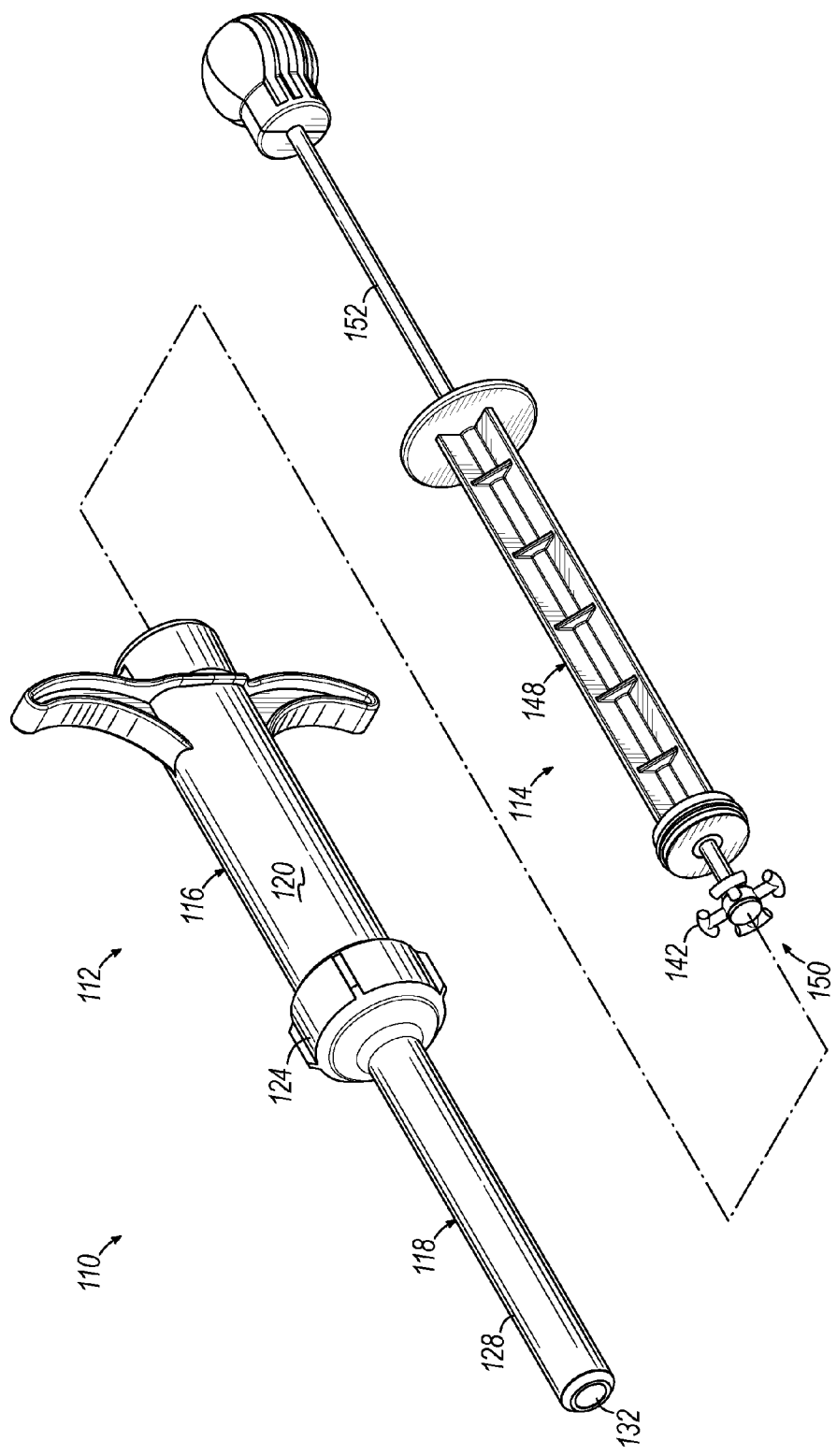
FIG. 6 is an isometric view showing the dispensing assembly of FIG. 5 partially disassembled, with a mixing and plunging assembly separated from a syringe body.
Figure 8B:
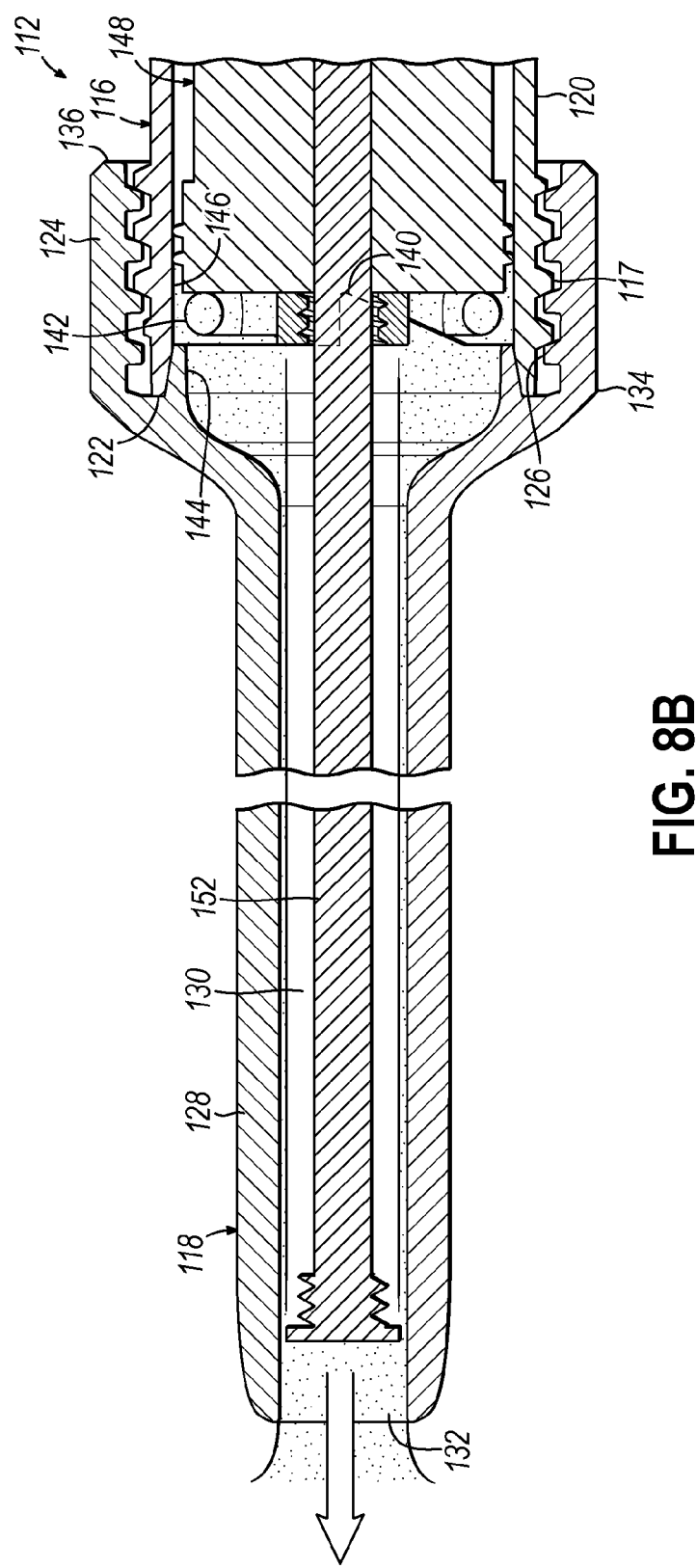

In addition, and as shown in FIGS. 3 and 3A, a mixing element engagement tab 44 is positioned within the syringe body 12 and is configured to engage with a mixing element of the mixing and plunging assembly 14, as will be described below. In particular, the engagement tab 44 is positioned in the barrel 16 near the distal end 20. In the embodiment shown, the engagement tab 44 extends from the interior surface 24 of the barrel 16 near the distal end 20 of the barrel 16 at the interior intersection of the barrel closure 42 and the barrel 16.

Figure 2:
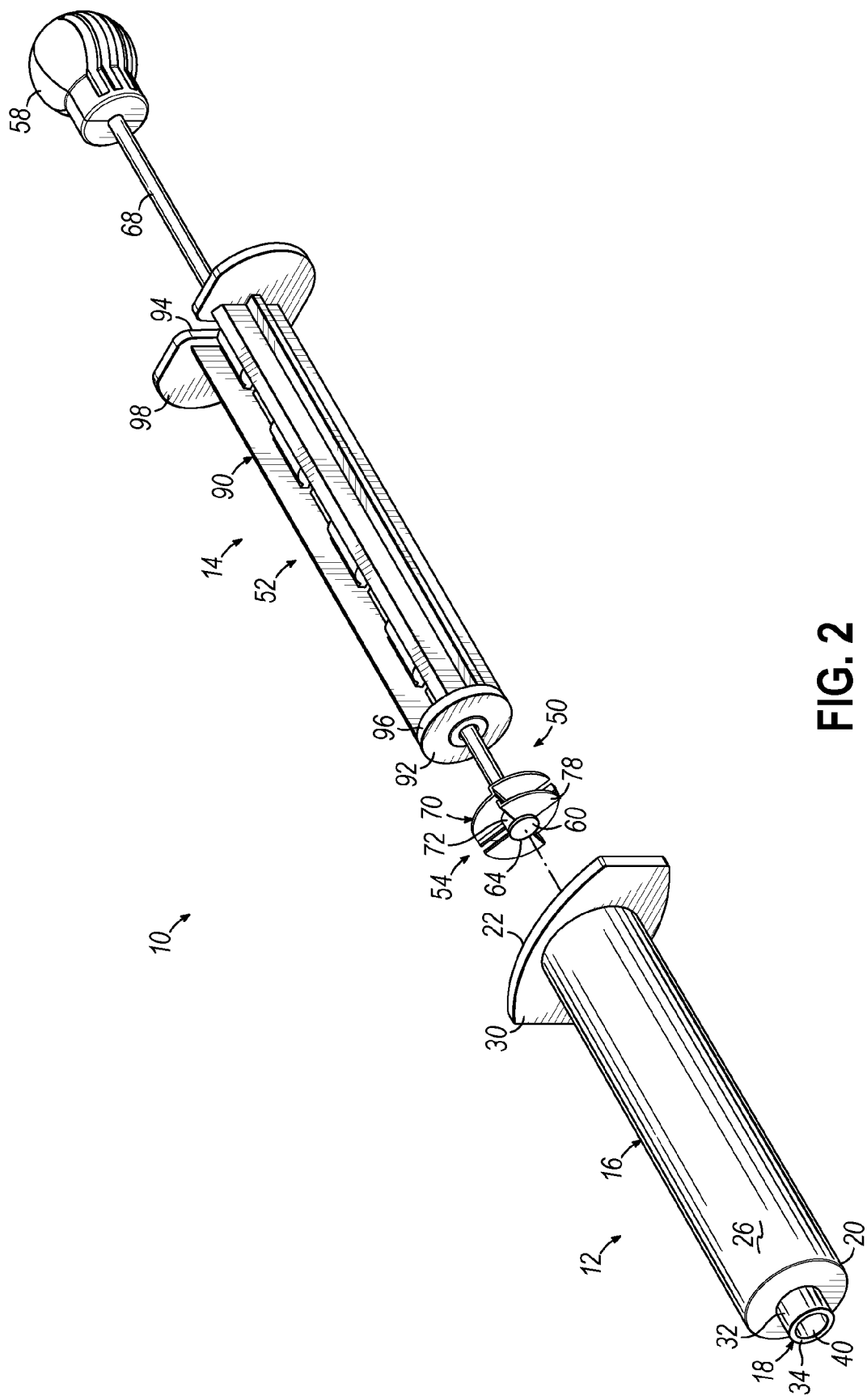
FIG. 2 is an isometric view showing the dispensing assembly of FIG. 1 partially disassembled, with a mixing and plunging assembly separated from a syringe body.

Referring next to FIGS. 2 and 3, the mixing and plunging assembly 14 generally includes a mixer 50 and a plunger 52. The assembly 14 is configured to be coupled with the syringe body 12, so that bone graft material therein can be dispensed from the syringe body 12. In addition, the mixer 50 is generally slidably and rotatably moveable with respect to the plunger 52, and the mixer 50 and can be used to mechanically agitate or mix material components within the barrel 16 of the assembled dispensing assembly 10. For example, the mixer 50 can be used to mix the material components of the bone graft material before it is dispensed from the dispensing assembly 10.

The mixer 50 includes a mixing element 54 removably connected with or attached to a rod 56, which can optionally include a handle 58. As will be apparent from the following description, the mixing element 54 is selectively attachable to and unattachable from the rod 56, and the rod 56 can be used to advance bone graft material out of the dispensing tip 18.

The rod 56 extends between a distal, or first, end 60 and an proximal, or second, end 62. In the embodiment shown, the rod 56 includes a head 64 at the distal end 60. The head 64 is generally solid and plate-shaped. The rod 56 further includes a threaded portion 66, which extends from the head 64, and a shaft 68. The threaded portion 66 may be formed on the shaft 68. As shown, the threaded portion 66 has a lesser diameter than the head 64, and the shaft 68 has a lesser diameter than the threaded portion 66. The handle 58 is attached to the shaft 68 near the proximal end 62 of the rod 56, and the handle 58 can be grasped by a user for manipulating the mixer 50.

The mixing element 54 is attached to the rod 56 by an attachment near the distal end 60 of the rod 56. The attachment is one that can be reversed so that the rod 56 is detached from the mixing element 54. In the embodiment shown, the attachment is a threaded attachment between components of the mixing element 54 and the rod 56. In particular, the mixing element 54 includes a body 70 having a generally centrally located hub 72, which includes a bore 74. The bore 74 includes a threaded portion 76 which is configured to mate with the threaded portion 66 of the rod 56 to form the attachment between the mixing element 54 and the rod 56. The body 70 also includes one or more vanes 78 that extend outwardly from the hub 72. The vanes 78 are configured to aid in the mixing of material components in the barrel 16.

The mixing element 54 is selectively attached to the rod 56 to form the attachment therebetween. In particular, the mixing element 54 is fed onto the rod 56 from the proximal end 62 of the rod 56, with the shaft 68 being inserted through the bore 74. The mixing element 54 is moved toward the distal end 60 of the rod 56, and the mixing element 54 is then threaded into attachment with the rod 56. In particular, the threaded portion 76 of the bore 74 of the mixing element 54 is threaded onto the threaded portion 66 of the rod 56. The mixing element 54 is completely threaded onto the threaded portion 66 when the mixing element 54 reaches and contacts the head 64. The mixing element 54 cannot be threaded past the head 64.

The mixing element 54 is selectively detached from the rod 56 by rotating the mixing element 54 relative to the rod 56 so that its threaded portion 76 is threaded off of the threaded portion 66 of the rod 56, at which point the between the mixing element 54 and the rod 56 is reversed, and there is no longer an attachment between those components. The mixing element 54 can be removed from the rod 56 by sliding it toward and off the proximal end 62 of the rod 56.

The plunger 52 is configured for dispensing bone graft material from the barrel 16 of the syringe body 12. In particular, the plunger 52 is configured for advancing bone graft material from the barrel 16 to the dispensing tip 18. The plunger 52 includes a body 90 that generally extends between a distal, or first, end 92 and an proximal, or second, end 94. The body 90 includes a plunging tip 96 at the distal end 92, which tip 96 is configured to be coupled with the barrel 16 in a generally conventional manner for dispensing bone graft material from the barrel 16. In particular, the tip 96 fits closely within the interior surface 24 of the barrel 16. The body 90 also includes a finger flange 98 at the proximal end 94, which flange 98 is configured for a user to press or pull during use of the plunger 52.

The body 90 also includes a passageway 100 extending therethrough. As shown, the passageway 100 extends through the flange 98, through the body 90 between the flange 98 and the tip 96, and through the tip 96. The passageway 100 is configured to receive the rod 56 of the mixer 50, and the passageway 100 is sized so as to allow slidable and rotatable movement of the rod 56 relative to the body 90. Advantageously, the passageway 100 is also sized to provide a close fit between the rod 56 and the tip 96, so as to prevent bone graft material from migrating from the barrel 16 into the passageway 100.

The mixer 50 is coupled with the plunger 52 by extending the rod 56 through the passageway 100. Thereby, the mixing and plunging assembly 14 is formed. For example, the rod 56 having the mixing element 54 attached thereto is inserted into the passageway 100 at the distal end 92 of the plunger body 90 and into the tip 96. The rod 56 is then further inserted through the body 90 so as to extend out of the passageway 100 and out of the flange 98 at the proximal end 94 of the body 90. In the assembled configuration, the mixing element 54 on the rod 56 is positioned on the side of the plunger body 90 near the plunging tip 96 and opposite the finger flange 98. After the mixing and plunging assembly is thus assembled, the handle 58 may be attached to the rod 56 near the proximal end 62 of the rod 56, generally opposite the mixing element 54.

The mixing and plunging assembly 14 is thereby configured for coupling with the syringe body 12. In particular, the end of the mixer 50 having the mixing element 54 and the end of the plunger 52 having the plunging tip 96 are inserted into the proximal end 22 of the barrel 16 of the syringe body 12. The plunging tip 96 forms a generally sealing, yet slidable, relationship with the interior surface 24 of the barrel 16. The mixing element 54 fits within the interior surface 24 of the barrel 16. The mixer 50 and the plunger 52 are slidably moveable within the barrel 16. In addition, the mixer 50 is rotatably moveable within the barrel 16. More specifically, the mixer 50 is free to slide and rotate in the barrel 16 relative to both the barrel 16 and the plunger 52.

The mixing and plunging assembly 14 can be coupled with the syringe body 12 after material components of the bone graft material are added to the barrel 16. For example, a liquid component and a solid component of the bone graft material can be added to the barrel 16, such as through the proximal end 22 thereof, and then the mixing and plunging assembly 14 can be coupled with the syringe body 12. The mixer 50 can then be used to mix the liquid and solid components within the barrel 16, thereby forming the bone graft material. As a further example, a solid component of the bone graft material can be added through the proximal end 22 of the barrel 16, and the plunger 52 can be used to draw a liquid component into the barrel 16 through the dispensing tip 18. The mixer 50 can then be used to mix the liquid and solid components, as discussed above.

Once the bone graft material is ready for dispensing, the mixing and plunging assembly 14 is used to discharge or dispense the bone graft material from the syringe body 12. In particular, the plunger 52 is moved in the direction of the distal end 20 of the barrel 16, and bone graft material within the barrel 16 is advanced toward the dispensing tip 18 and through the dispensing opening 40 of the dispensing tip tube 32. The plunger 52 continues to advance bone graft material out of the barrel 16 until the plunger 52 is completely depressed in the barrel 16. In that position, the plunger tip 96 is generally at its forward-most location in the barrel 16, which is generally near the barrel distal end 20. Even once all the bone graft material has been discharged from the barrel 16, a volume of bone graft material still occupies the dispensing tip tube 32.

The rod 56 of the mixer 50 is detached from the mixing element 54 and is used to dispense the bone graft material from the dispensing tip 18. In particular, when the plunger 52 is near its forward-most location in the barrel 16, the mixing element 54 is generally near the barrel distal end 20, which is where the mixing element engagement tab 44 is positioned. The mixer 50 is moved so as to longitudinally align the engagement tab 44 with the mixing element 54, and then the rod 56 is rotated. The mixing element 54 comes into contacting engagement with the engagement tab 44, and continued rotation of the rod 56 while the mixing element 54 is held still by the engagement tab 44 causes relative rotation between the rod 56 and the mixing element 54. Thereby, the threaded portion 66 of the rod 56 is rotated relative to the threaded portion 76 of the mixing element 54, and the rod 56 is detached from the mixing element 54.

Once the rod 56 is detached from the mixing element 54, the rod 56 can be moved to dispense additional amounts of bone graft material from the syringe body 12. In particular, the rod 56 is moved past the distal end 20 of the barrel 16 and into the dispensing tip 18. More specifically, the head 64 of the rod 56 is advanced into the dispensing tip tube 32, beginning at the proximal end 36 thereof. Bone graft material contained within the dispensing passageway 38 is pushed by the head 64 of the rod 56 out of the dispensing opening 40. The rod 56 is further pushed toward the distal end 34 of the dispensing tip tube 32, and the head 64 advances the bone graft material contained within the passageway 38 of the tube 32 out of the dispensing opening 40.

Advantageously, the head 64 is sized to fit closely within the dispensing passageway 38 so as maximize the amount of bone graft material that can be pushed from the dispensing tip tube 32 by the rod 56. Thereby, the rod 56 is used to dispense additional amounts of bone graft material from the syringe body 12, and performs a similar function as a stylet for pushing bone graft material out of the dispensing tip 18. This reduces the amount of bone graft material that would otherwise remain in the syringe body 12, and in particular in the dispensing tip 18, and be wasted during a bone graft material dispensing operation. The rod 56 can have any appropriate length, and can be sufficiently long to extend through the dispensing opening 40 of the dispensing tip 18, or can be sufficiently short so that it does not reach the dispensing opening 40.

Referring next to FIGS. 5-8B, a dispensing assembly 110 constructed according to a further embodiment of the invention is shown. The dispensing assembly 110 includes a syringe body 112 and a mixing and plunging assembly 114. The mixing and plunging assembly 114 is generally similar to the mixing and plunging assembly 14 discussed above with respect to the dispensing assembly 10. The syringe body 112 includes a barrel 116 and a dispensing tip 118, which is selectively attachable to and removable from the barrel 116. In particular, the barrel 116 includes a threaded portion 117 on an exterior surface 120 and near a distal end 122 of the barrel 116.

The dispensing tip 118 is attachable to the barrel 116. In particular, the dispensing tip 118 includes an attachment portion 124 that is sized to be received over the distal end 122 of the barrel 116. The attachment portion 124 includes a radially interior threaded portion 126 that is configured to threadably mate with the threaded portion 117 of the barrel 116. The dispensing tip 118 further includes a dispensing tip tube 128 connected with the attachment portion 124. The dispensing tip tube 128 includes a dispensing passageway 130 that opens at a dispensing opening 132 for dispensing bone graft material. The dispensing tip tube 128 has a reduced diameter as compared with the barrel 116. As discussed above with respect to the dispensing tip 18, the dispensing tip 118 may also be referred to as a cannulus or cannulus device, and can have any suitable length.

The attachment portion 124 extends between a distal, or first, end 134 and an proximal, or second, end 136. The threaded portion 126 of the attachment portion 124 is generally between the ends 134, 136. The dispensing tip 118 is attached to the barrel 116 by threading the threaded portion 126 of the attachment portion 124 onto the threaded portion 117 of the barrel 116. In particular, the threaded portion 126 of the attachment portion 124 is threaded onto the threaded portion 117 of the barrel 116 until a distal end 122 of the barrel 116 is positioned generally near the distal end 134 of the attachment portion 124.

The dispensing tip 118 includes one or more mixing element engagement tabs 140 for engaging with a mixing element 142 of the mixing and plunging assembly 114. In particular, the dispensing tip 118 includes a neck 144 radially inside the threaded portion 126 of the attachment portion 124. The neck 144 is configured to fit radially inside an interior surface 146 of the barrel 116 near the barrel distal end 122 when the dispensing tip 118 is attached to the barrel 116. In the embodiment shown, two engagement tabs 140 extend from the neck 144 at diametrically opposed locations, and are configured to be situated within the barrel 116 near the distal end 122 thereof when the dispensing tip 118 is attached to the barrel 116. The engagement tabs 140 perform a similar function to the engagement tab 44 discussed above.

The dispensing assembly 110 is used in a manner generally similar to the dispensing assembly 10. In particular, once the plunger 148 of the mixing and plunging assembly 114 is completely depressed in the barrel 116 and is moved to its forward-most location in the barrel 116, the mixing element 142 is generally near the barrel distal end 122. Again the mixing element engagement tabs 140 are positioned in the barrel 116 near the distal end 122. The mixer 150 of the mixing and plunging assembly 114 is moved so as to longitudinally align the engagement tabs 140 with the mixing element 142, and then the rod 152 of the mixer 150 is detached from the mixing element 142. In particular, the rod 152 is rotated relative to the syringe body 112 and the mixing element 142 comes into contacting engagement with one or more of the engagement tabs 140. Continued rotation of the rod 152 while the mixing element 142 is held still by the engagement tabs 140 causes the rod 152 to become detached from the mixing element 142, in a similar manner as discussed above.

Once the rod 152 is detached from the mixing element 142, it is moved to dispense additional amounts of bone graft material from the syringe body 112 in a similar manner as discussed above. In particular, the rod 152 is moved into the dispensing passageway 130 of the dispensing tip 118, and bone graft material contained within the dispensing passageway 130 is pushed out of the dispensing opening 132.

Since the dispensing tip 118 is easily removed from the barrel 116, the dispensing tip 118 can be removed from the barrel 116 to introduce bone graft material, or components thereof, into the barrel 116. For example, the dispensing tip 118 can be removed, and an adapter device (not shown) can be attached to the barrel 116 to facilitate the introduction of material into the barrel 116 in a generally known manner.

Figure 9A:
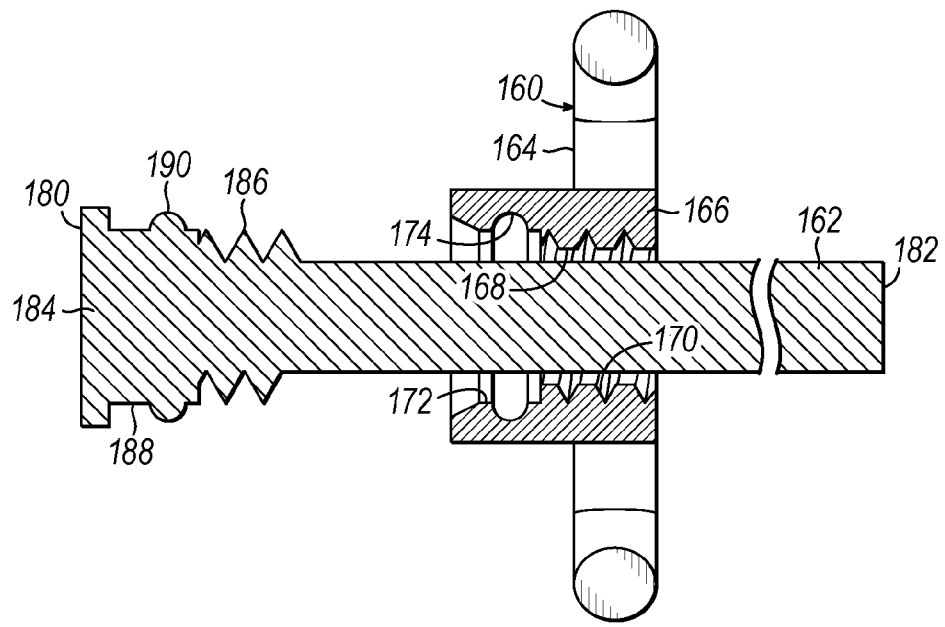
FIGS. 9A and 9B are cross-sectional views showing features for forming a snap-fit attachment between a rod and a mixing element according to another embodiment of the invention.
Figure 9B:
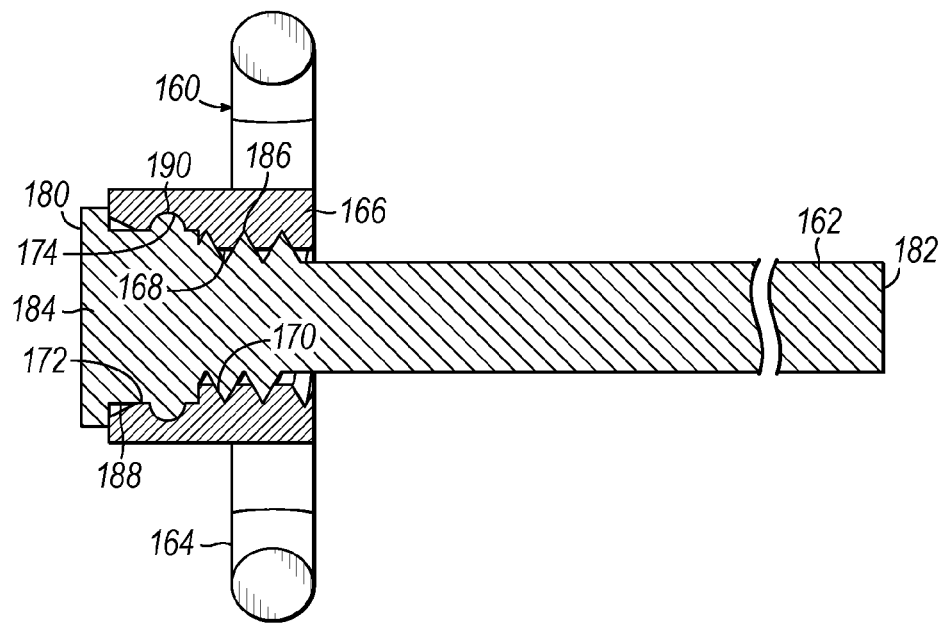

Referring next to FIGS. 9A and 9B, additional features can be provided that relate to the connection between a mixing element and a rod. In the embodiments discussed above, the attachment between the mixing elements 54, 142 and the rods 56, 152 is made through a threaded attachment. In addition to such a threaded attachment, features can also be provided to create a snap-fit attachment between a mixing element and a rod, as shown with respect to the exemplary mixing element 160 and rod 162.

The mixing element 160 includes a body 164 having a centrally located hub 166. A bore 168 extends through the hub 166 and includes a threaded portion 170. The bore 168 also includes a snap attachment portion 172 having an annular groove 174 for receiving a component on the rod 162.

The rod 162 extends between a distal, or first, end 180, and an proximal, or second, end 182. The rod 162 includes a head 184 at the distal end 180. The rod 162 also includes a threaded portion 186 configured to be mated with the threaded portion 170 of the mixing element 160. The rod 162 further includes a snap attachment portion 188 situated generally between the head 184 and the threaded portion 186. The snap attachment portion 188 includes one or more nubs or protrusions 190 configured to be received in the annular groove 174 of the snap attachment portion 172 of the mixing element 160.

The mixing element 160 and rod 162 are thus attachable by both a threaded attachment and a snap-fit attachment. In particular, the mixing element 160 is placed onto the rod 162 and moved toward the head 184 of the rod 162. The mixing element 160 is oriented so that the snap attachment portion 172 is positioned generally between the threaded portion 170 and the head 184 of the rod 162. The threaded portion 170 of the mixing element 160 is threaded onto the threaded portion 186 of the rod 162. As the mixing element 160 is nearly completely threaded onto the rod 162, the snap attachment portions 172, 188 become generally aligned, and the protrusions 190 extend into the annular groove 174. Thereby, a snap-fit attachment is also formed between the mixing element 160 and the rod 162.

The mixing element 160 is detached from the rod 162 in the reverse manner. In particular, the mixing element 160 is rotated relative to the rod 162 so that the threaded portion 170 on the mixing element 160 is threaded off of the threaded portion 186 of the rod 162. At the same time, the protrusions 190 are moved away, and removed, from the annular groove 174, and the snap-fit attachment is overcome.

Optionally, the mixing element 160 and the rod 162 can include features designed to prevent material from being trapped between the mixing element 160 and the rod 162 are attached to one another. In particular, at least one or both of the mixing element 160 and the rod 162 can include vent grooves that allow material to escape being trapped. In the embodiment shown, the mixing element 160 includes one or more longitudinally extending vent grooves 192 that extend from the annular groove 174 to a forward portion of the hub 166. In addition, the rod 162 includes one or more longitudinally extending vent grooves 194 that extend from the protrusions 190 to the distal end 180 of the rod 162. The grooves 192, 194 provide passageways for material to move in when the mixing element 160 is attached with the rod 162 in the manner discussed above. Thereby, the material is not trapped between the mixing element 160 and the rod 162 and can escape through the grooves 192, 194.

Referring next to FIGS. 10A, 10B, 11A, and 11B, additional features can be provided that relate to the connection between a rod and a plunger. In the embodiments discussed above, the rods 56, 152 are entirely free to slidably move with respect to the plungers 52, 148. Features can be provided to limit the slidable movement of a rod with respect to a plunger. In particular, an attachment can be provided for limiting the movement of a rod with respect to a plunger.

Figure 10A:
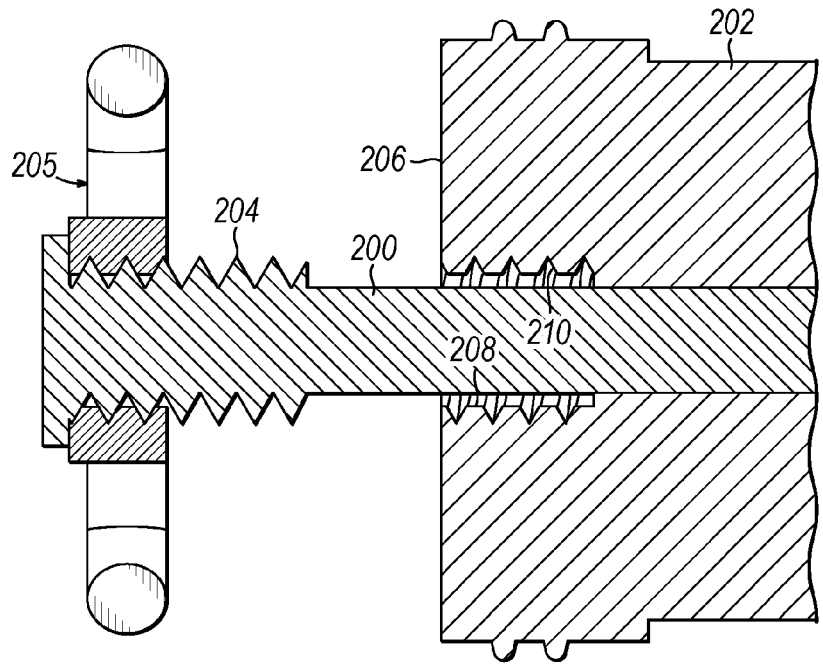
FIGS. 10A and 10B, and 11A and 11B are cross-sectional views showing features for limiting the slidable movement of a rod with respect to a plunger according to further embodiments of the invention.
Figure 10B:
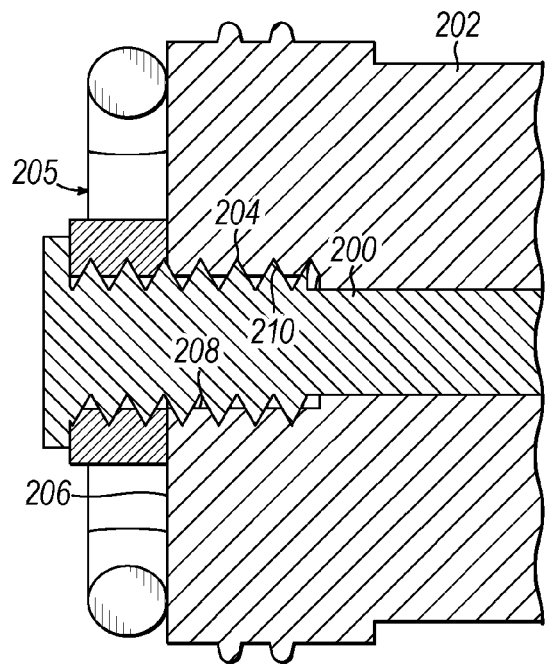

In particular, and as shown with respect to the rod 200 and plunger 202 shown in FIGS. 10A and 10B, a threaded attachment can be provided to limit the slidable movement of the rod 200 relative to the plunger 202. In particular, the rod 200 includes an extended threaded portion 204 that is sized so that the threaded portion 204 extends beyond a mixing element 205 once the mixing element is attached to the threaded portion 204, such as in the manner discussed above with respect to the dispensing assembly 10. The threaded portion 204 that extends beyond the mixing element is used to attach the rod 200 with the plunger 202.

In particular, the plunger 202 includes a plunger tip 206 having an opening 208 that receives the rod 200. The opening 208 includes a threaded portion 210 that is configured to mate with the threaded portion 204 of the rod 200.

The rod 200 can thereby be selectively attached and detached from the plunger 202, wherein in the attached configuration, slidable movement of the rod 200 with respect to the plunger 202 is limited. In particular, the threaded portion 204 of the rod 200 is threaded into the threaded portion 210 of the opening 208 of the plunger tip 206 to put the rod 200 in the attached configuration. The threaded portion 204 of the rod 200 is threaded out of the threaded portion 210 of the opening 208 of the plunger tip 206 to put the rod 200 in the detached configuration.

Figure 11A:
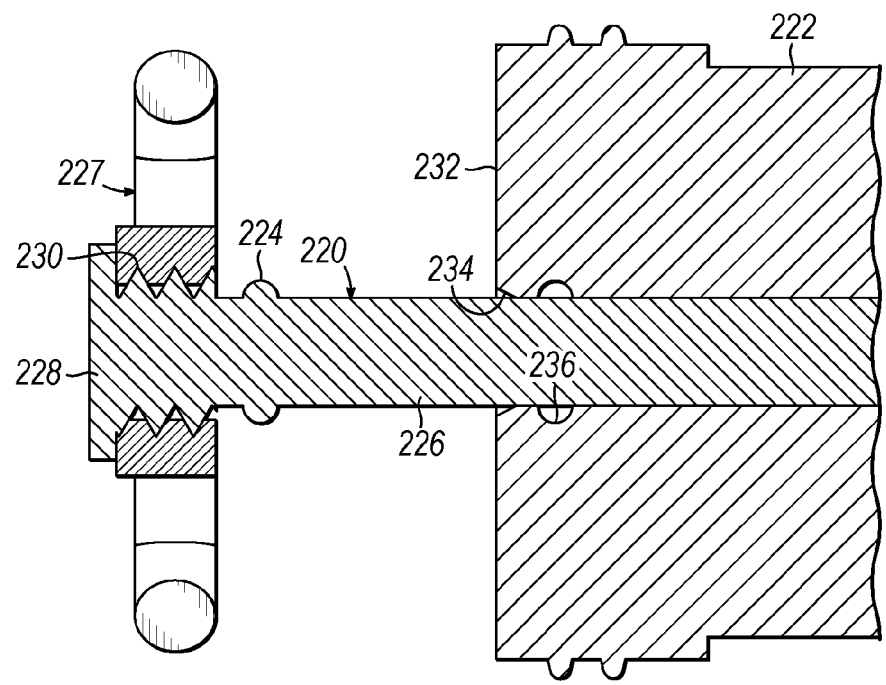
Figure 11B:
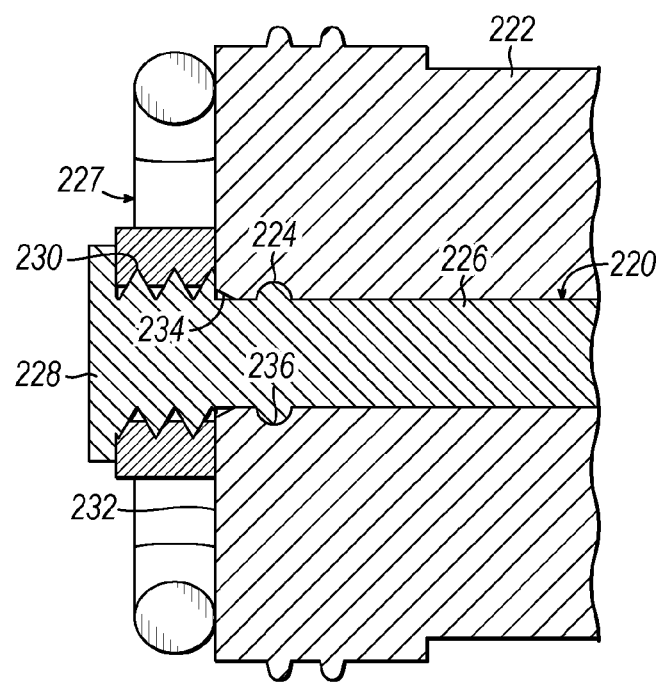
Figure 12:
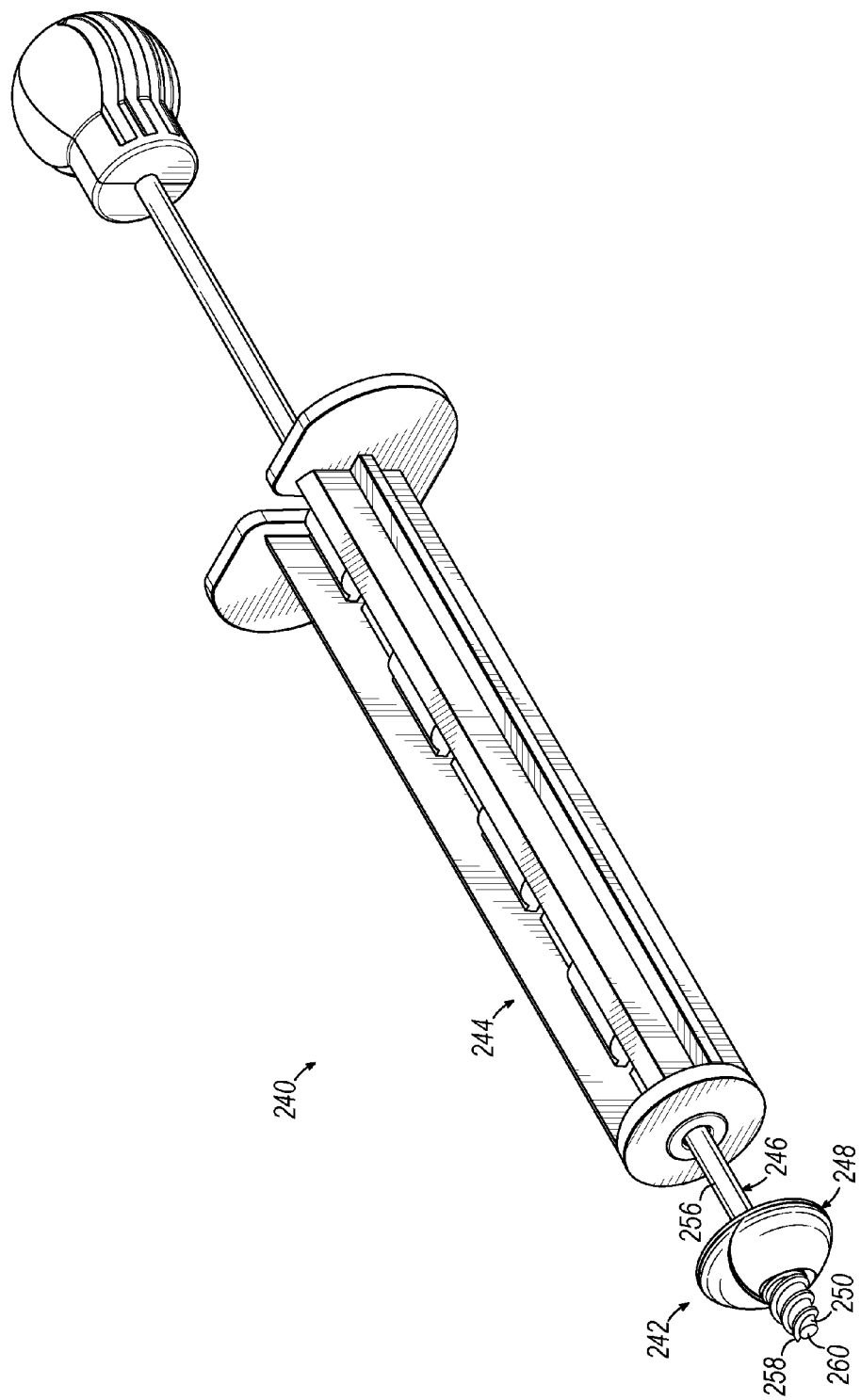
FIG. 12 is an isometric view showing a mixing and plunging assembly according to another embodiment of the invention.

Referring next to FIGS. 11A and 11B, a snap-fit attachment can be provided to limit the slidable movement of a rod 220 relative to a plunger 222. In particular, the rod 220 includes one or more nubs or protrusions 224 on a shaft 226 of the rod 220. The rod 220 also includes a head 228 and a threaded portion 230, and the threaded portion 230 is generally positioned between the head 228 and the protrusions 224 on the shaft 226. The protrusions 224 are oriented on the shaft 226 so as to be accessible on the shaft 226 even once a mixing element 227 is attached to the threaded portion 230 of the rod 220, such as in a similar manner as discussed above with respect to the dispensing assembly 10. The protrusions 224 are configured to be received in a corresponding feature of the plunger 222.

The plunger 222 includes a plunger tip 232 having an opening 234 that receives the rod 220. The opening 234 includes an annular groove 236 that is configured to receive the protrusions 224 of the rod 220.

The rod 220 can thereby be selectively attached and detached from the plunger 222, wherein in the attached configuration, slidable movement of the rod 220 with respect to the plunger 222 is limited. In particular, the rod 220 is moved so that the protrusions 224 of the rod 220 are positioned in the groove 236 of the opening 234 of the plunger tip 232 to put the rod 220 in the attached configuration. The rod 220 is moved with respect to the plunger 222 so that the protrusions 224 are moved out of the groove 236 to put the rod 220 in the detached configuration.

These optional features that relate to the connection between a mixing element and a rod, and to limiting the slidable movement of a rod with respect to a plunger can be combined in any possible manner, including having none, any, or several of the above described features. For example, an embodiment could be provided that includes both a snap-fit attachment between a mixing element and a rod, and either a threaded or a snap-fit attachment between a rod and a plunger.

Referring next to FIGS. 12 through 15, additional optional features are shown that can be incorporated into dispensing assemblies, such as the dispensing assemblies 10 and 110. Beginning with FIGS. 12 and 13, a mixing and plunging assembly 240 includes a mixer 242 and a plunger 244. The mixer 242 includes a rod 246 and a mixing element 248.

The rod 246 includes an auger tip 250, a head 252, a threaded portion 254, and a shaft 256. The auger tip 250 is configured for engagement with material in a syringe body, such as bone graft material, or the components of bone graft material. The auger tip 250 extends forwardly from the head 252 so that it extends generally beyond the mixing element 248. In the embodiment shown, the auger tip 250 has a generally conical shape with blades or flighting 258 extending therealong, and includes a generally pointed end 260.

The pointed end 260 and the flighting 258 engage material when the mixer 242 is slidably and rotatably moved in a syringe body.

The mixing element 248 includes a body 262 having a centrally located hub 264, which includes a threaded bore 266. The threaded bore 266 allows the mixing element 248 to be attached to the threaded portion 254 of the rod 246. The body 262 of the mixing element 248 also includes vanes 268 that extend outwardly from the hub 264, and the vanes 268 are configured for engaging material in a syringe body. In the embodiment shown, each vane 268 includes a cutting surface 270.

The body 262 extends generally between a distal, or first, end 272 and an proximal, or second, end 274. In addition to extending outwardly from the hub 264, the vanes 268 extend generally in the direction from the distal end 272 toward the proximal end 274. The vanes 268 define leading edges 276 of the mixing element 248, and the cutting surfaces 270 are positioned generally on the leading edges 276. The leading edges 276 give the mixing element 282 a profile, or shape, that is configured to be generally complementary to the shape of a portion of the interior of a syringe body.

Figure 13:
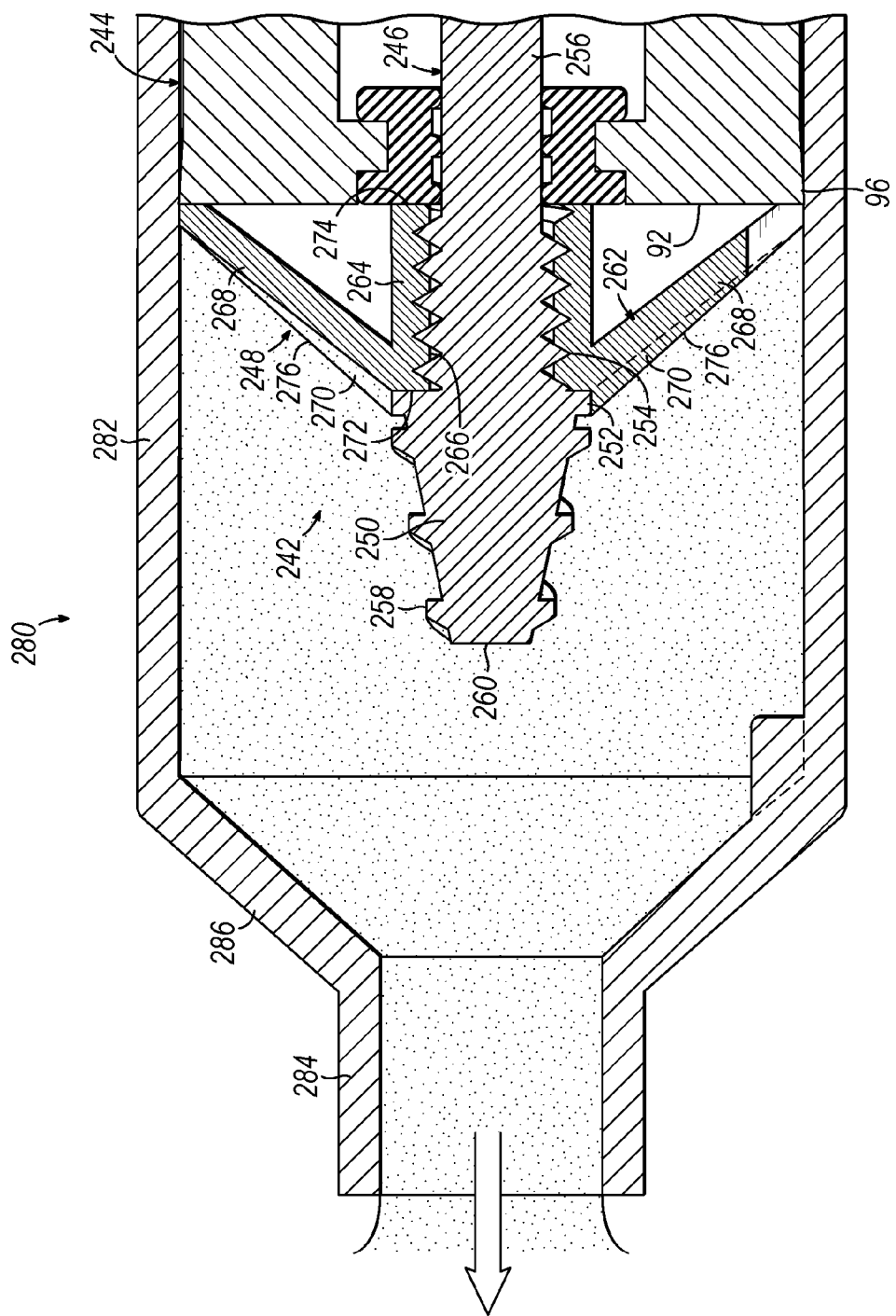
FIG. 13 is a cross-sectional view similar to FIG. 4A and showing the mixing and plunging assembly used in a syringe body to dispense bone graft material.

For example, and as shown in FIG. 13, a syringe body 280 includes a barrel 282 and a dispensing tip 284, which are connected by a barrel closure 286. The barrel closure 286 forms an angle relative to a longitudinal axis of the barrel 282 that is generally complementary with an angle formed by the vanes 268 and the leading edges 276 relative to the longitudinal axis of the barrel 272. Thereby, the leading edges 276 of the mixing element 242 have a shape that is generally complementary with the interior shape of the syringe body 280 near the connection of the barrel 282 and the dispensing tip 284.

Advantageously, when the mixing and plunging assembly 240 is moved to its forward-most location in the barrel 272, the mixing element 248 generally abuts the syringe body 280 near the connection of the barrel 282 and the dispensing tip 284. In particular, the leading edges 276 of the mixing element 248 will abut the barrel closure 286. Such a complementary shaped configuration between the mixing element 248 and the syringe body 280 encourages material in the barrel 282 to be moved into the dispensing tip 284, thereby minimizing the amount of material that would otherwise remain in the barrel 282 and be wasted.

The embodiment shown in FIG. 13 includes an integrally formed barrel 282, dispensing tip 284, and barrel closure 286, similar to what is shown in FIGS. 1-4C. It will be appreciated, though, that a complementary shaped configuration between a mixing element and the interior shape of a syringe body is also applicable to a syringe body where the dispensing tip is selectively attachable to and removable from a barrel, such as shown in FIGS. 5-8B.

Figure 14:
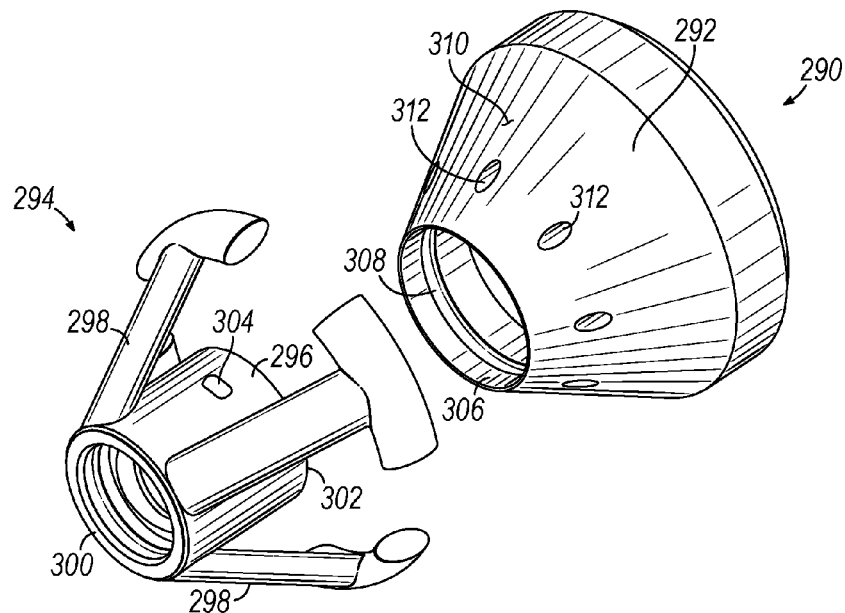
FIGS. 14 and 15 are isometric views showing plunging tips and associated mixing elements according to further embodiments of the invention.
Figure 15:
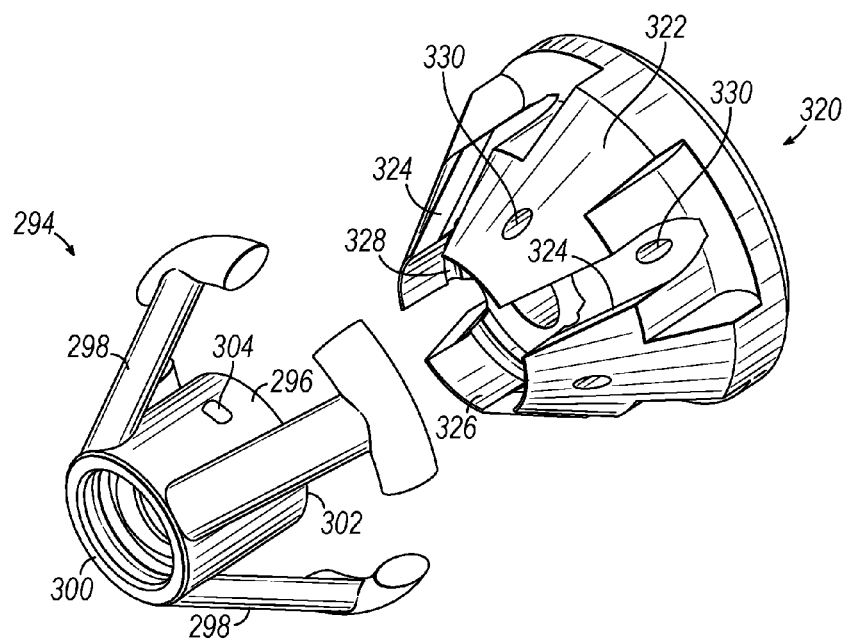
Figure 16:
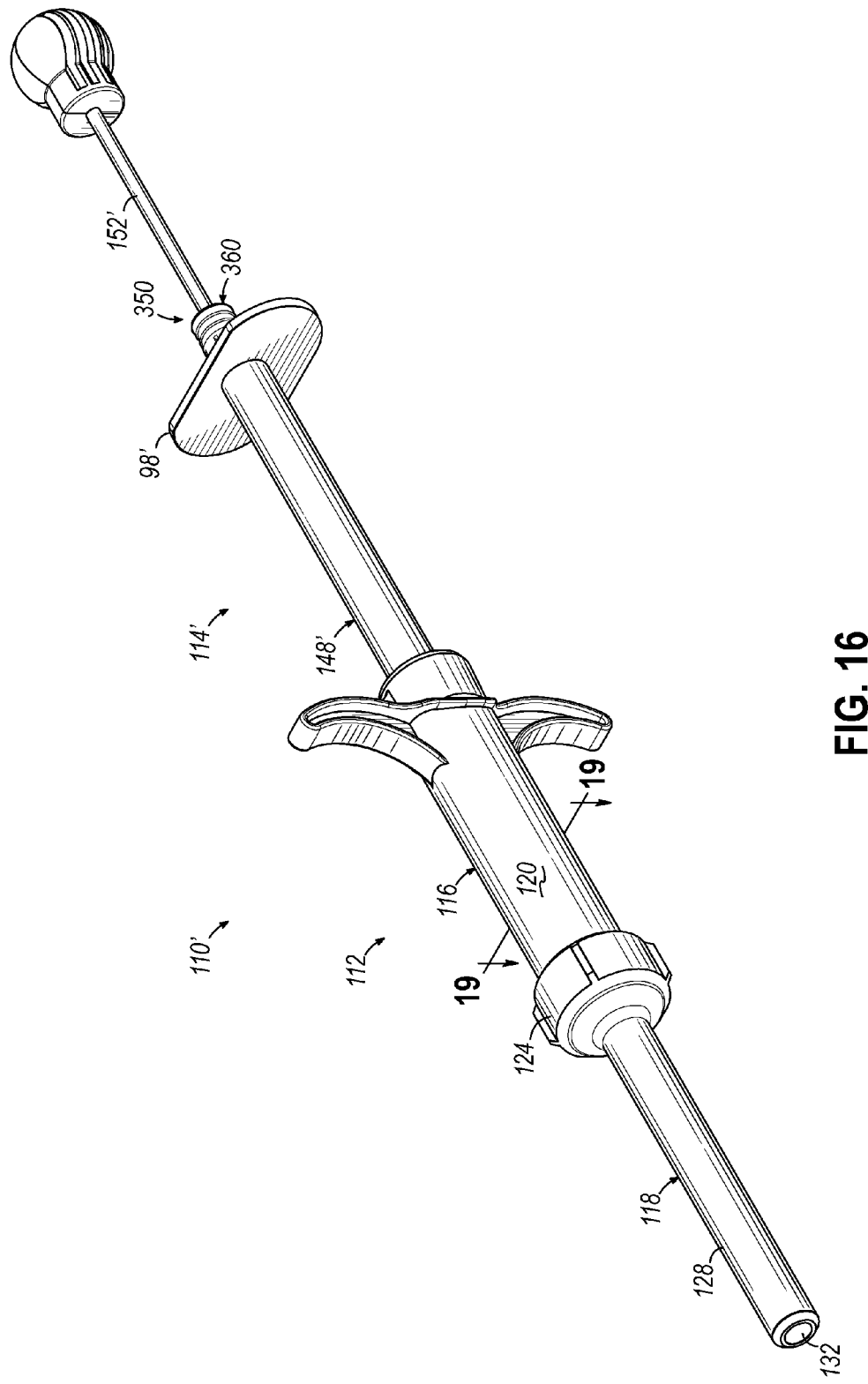
FIG. 16 is an isometric view showing a dispensing assembly constructed according to another embodiment of the present invention.
Figure 17:
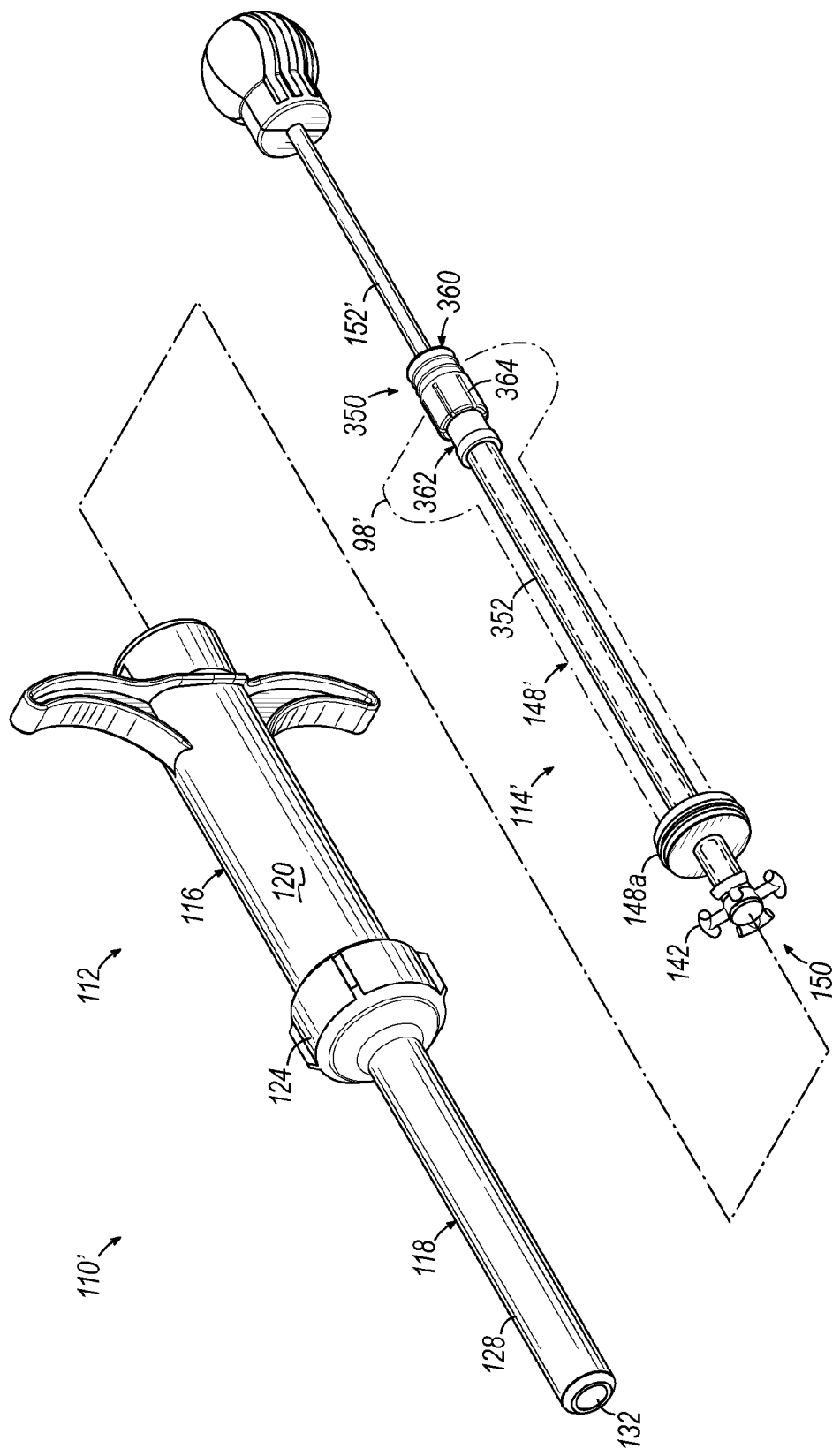
FIG. 17 is an isometric view showing the dispensing assembly of FIG. 16 partially disassembled, with a mixing and plunging assembly separated from the syringe body.
Figure 18:
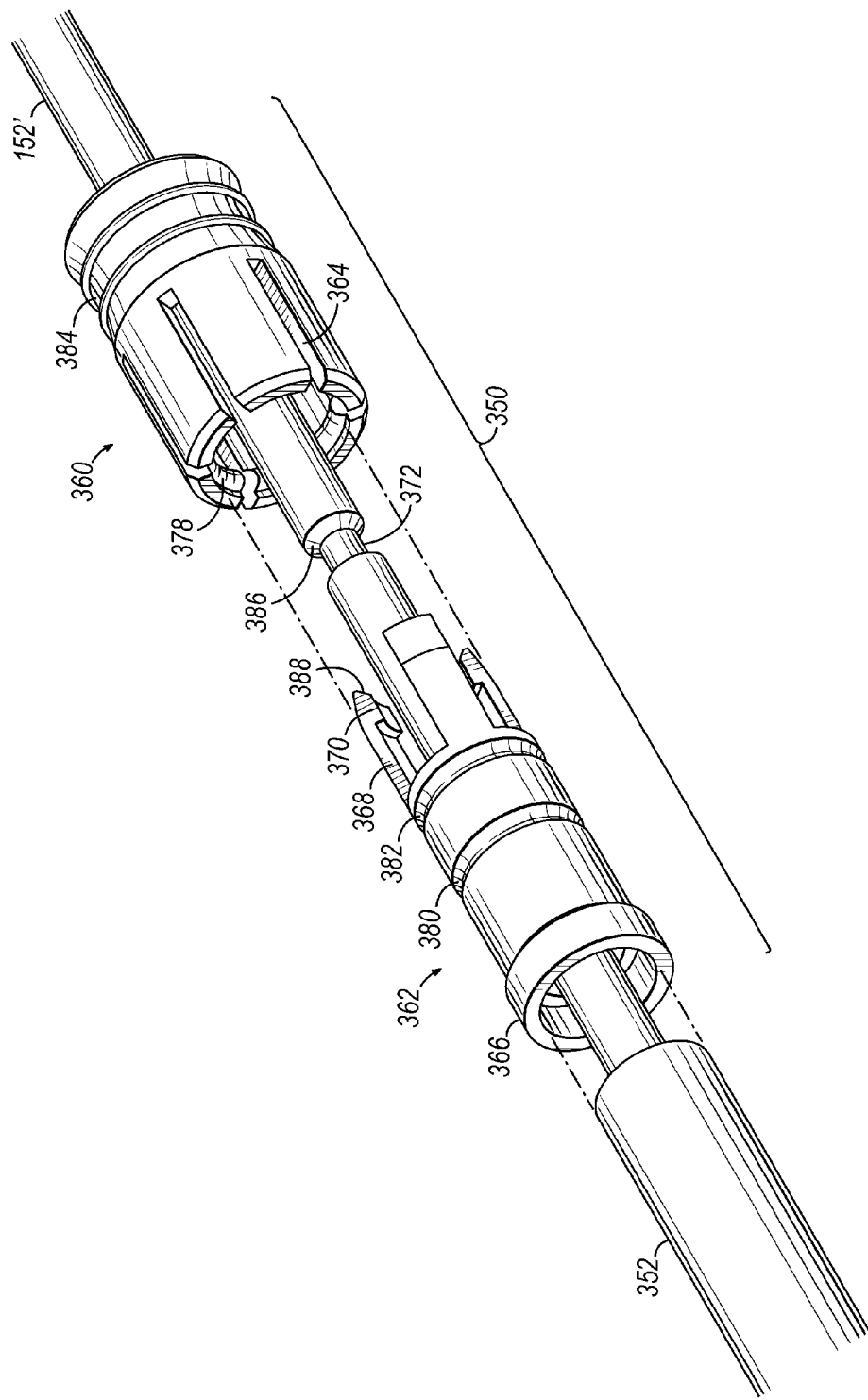
FIG. 18 is an isometric, enlarged view showing a connector assembly for selectively connecting a rod of the mixer to the mixing element.

Referring next to FIGS. 14 and 15, alternative plunging tip configurations are shown. Some plunging tips, such as those discussed above with respect to plungers 52 and 148 and shown in the related figures, have front surfaces that extend generally perpendicularly to the longitudinal axes of the plungers. FIGS. 14 and 15, on the other hand, show plunging tips having different configurations.

FIG. 14 shows a plunging tip 290 that has a generally frusto-conically shaped body 292. The plunging tip 290 is configured to be incorporated in a plunger, and is also configured to have a shape that generally matches the shape of an associated mixing element 294.

The mixing element 294 includes a centrally located hub 296 and vanes 298 extending outwardly therefrom. The vanes 298 are configured to engage material in a syringe body of a dispensing assembly, like the vanes of the mixing elements discussed above. The vanes 298 extend generally in the direction from a distal, or first, end 300 of the hub 296 toward an proximal, or second, end 302 of the hub 296. Thus, the vanes 298 extend generally at an angle with respect to a longitudinal axis of the hub 296. The hub 296 also includes nubs or protrusions 304 that are configured to be received in a corresponding feature of the plunging tip 290.

The body 292 of the plunging tip 290 includes a bore 306 configured to partially receive the mixing element 294. An annular groove 308 is included in the bore 306 and is configured to receive the protrusions 304 of the mixing element 294. The body 292 includes a generally solid and sloped outer surface 310. The outer surface 310 is oriented relative to a longitudinal axis of the body 292 at approximately the same angle that the vanes 298 extend with respect to the longitudinal axis of the hub 296.

The mixing element 294 and the plunging tip 290 are configured to be selectively coupled together. In particular, the hub 296 of the mixing element 294 is configured to be received in the bore 306 of the plunging tip 290 in the relative orientations shown in FIG. 14. The mixing element 294 and the plunging tip 290 are brought together until the protrusions 304 on the hub 296 are received in the annular groove 308 of the plunging tip 290. When the mixing element 294 and the plunging tip 290 are thus coupled, the vanes 298 extend along the outer surface 310 of the plunging tip 290 in close relationship thereto. Thereby, the shape of the mixing element 294 generally matches the shape of the plunging tip 290. Advantageously, the vanes 298 abut the outer surface 310 when the mixing element 294 and the plunging tip 290 are coupled together.

Optionally, the plunging tip 290 includes bores 312 that extend generally longitudinally through the body 292. The bores 312 are configured to allow air to escape past the plunging tip 290. In particular, the bores 312 intersect the outer surface 310 and extend through the body 292 to allow air to pass from the side of the plunging tip 290 having the outer surface 310 to the other side.

Turning to FIG. 15, a plunging tip 320 is shown and is associated with the same mixing element 294 discussed above and shown in FIG. 14. The plunging tip 320 is generally similar to the plunging tip 290, but includes a body 322 having recesses or slots 324 for partially or completely receiving features of the mixing element 294. In particular, the slots 324 are configured to receive the vanes 298 of the mixing element 294. The mixing element 294 and the plunging tip 320 are configured to be selectively coupled together. In particular, the plunging tip has a bore 326 and the hub 296 of the mixing element 294 is configured to be received in the bore 296. The plunging tip 320 also includes an annular groove 328. The mixing element 294 and the plunging tip 320 are brought together so that the vanes 298 are received in the slots 324 and the protrusions 304 are received in the annular groove 328. Thereby, the shape of the mixing element 294 generally matches the shape of the plunging tip 320, and the mixing element 294 partially fits within the body 322 of the plunging tip 320 when the mixing element 294 and plunging tip 320 are coupled together.

Optionally, the plunging tip 320 includes bores 330 that extend generally longitudinally through the body 322. The bores 330 serve a similar function as the bores 312 discussed above with respect to FIG. 14. As shown, some of the bores 330 intersect the slots 324.

According to even further embodiments of the invention, a dispensing assembly can be provided that includes a syringe body and a plunging assembly. The syringe body includes a barrel and a dispensing tip. The plunging assembly is configured for coupling with the syringe body and includes a plunger and a rod. The plunger is configured to dispense material from the barrel through the dispensing tip. The rod is configured to be moved relative to the plunger and the syringe body into the dispensing tip to push material out of the dispensing tip. The plunger can include a passageway that receives the rod. In addition, the plunger and rod can be configured to selectively limit the slidable movement of the rod with respect to the plunger. In some embodiments, the rod is detached from the plunger before the rod is pushed into the dispensing tip.

Advantageously, the assemblies disclosed herein can be used for dispensing other types of materials than bone graft material, such as other biomaterials, or other materials, generally, that would benefit.

FIGS. 16-21 illustrate a dispensing assembly 110' constructed according to another embodiment of the invention. In this embodiment, new reference numerals are used to describe new elements of structure, while the same reference numerals are used to describe like structure previously shown and described in connection with FIGS. 5-8B. Those reference numerals having prime marks (') refer to elements of structure that correspond to like numbered, previously described elements in the embodiments of FIGS. 5-8B. However, the elements with reference numerals having prime marks will have slightly different form and/or function from the previously described elements and such differences will either be described hereinbelow or will be evident from a review of the drawings themselves. Generally, those elements that are identical to previously described structure will not be discussed hereinbelow, but the previous discussion may be referred to instead.

Figure 20A:
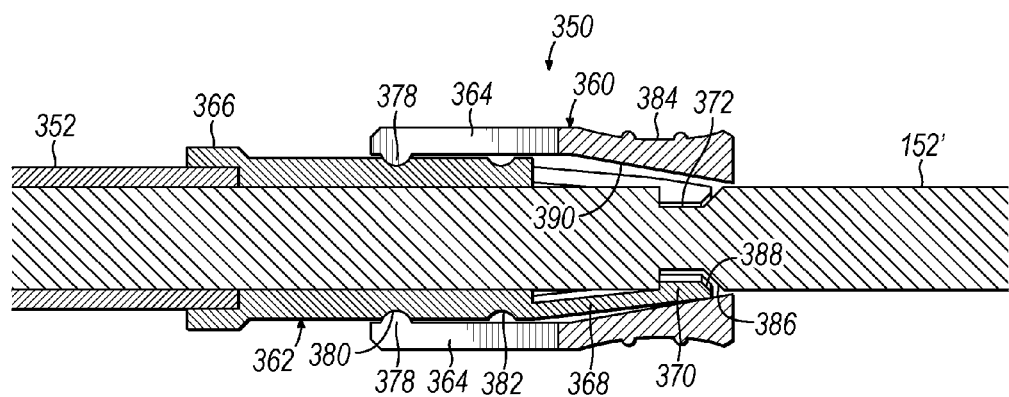
FIGS. 20A and 20B are respective cross sectional views showing the connected and disconnected conditions of the connector assembly used to connect the rod of the mixer to the mixing element.
Figure 20B:
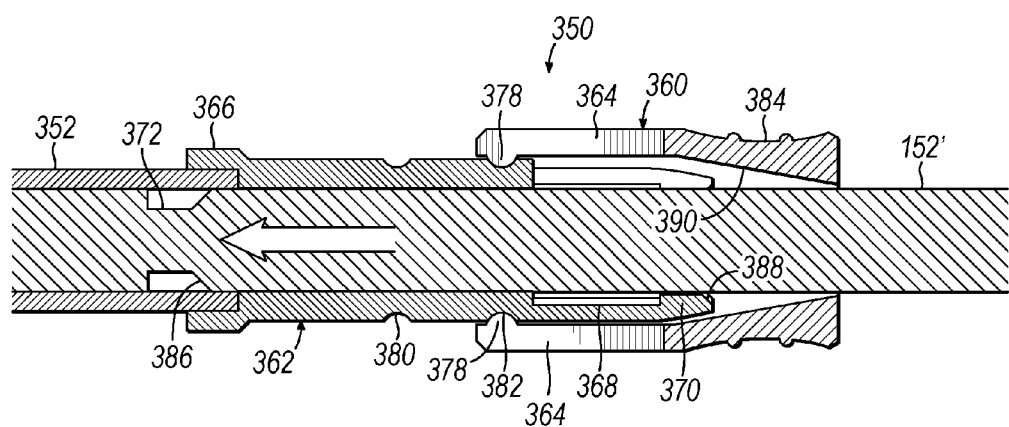

The main difference between the embodiment of FIGS. 16-21 and the previously described embodiment of FIGS. 5-8B is in the connection between the mixer rod 152' and the plunger 148'. Referring particularly to FIGS. 17, 18, 20A and 20B, the connection is made at a proximal location on the assembly 110' as opposed to being made at the distal end, i.e., at the mixing element 142. The proximal location is preferably outside of the barrel 116. A connector assembly 350 is used to connect the mixer rod 152' for a translational and rotational movement with the mixing element 142 via a hollow shaft 352. Specifically, the connector assembly 350 is used to ensure that the mixer rod 152' will travel back and forth with the hollow shaft 352 as the mixing element 142 is translated linearly within the syringe barrel 116 as shown in FIG. 20. To transfer torque or rotational movement of the mixer rod 152' to the mixing element 142, keys 354 (only one shown) are formed at the distal end of the mixer rod 152' and are received within key ways 356 at the distal end of the hollow shaft 352. The distal end of the hollow shaft 352 is rigidly coupled to the mixing element 142. Thus, they keys 354 ensure that when the mixer rod 152' is rotated, the hollow shaft 352 and the attached mixing element 142 rotate as well.

Figure 21:
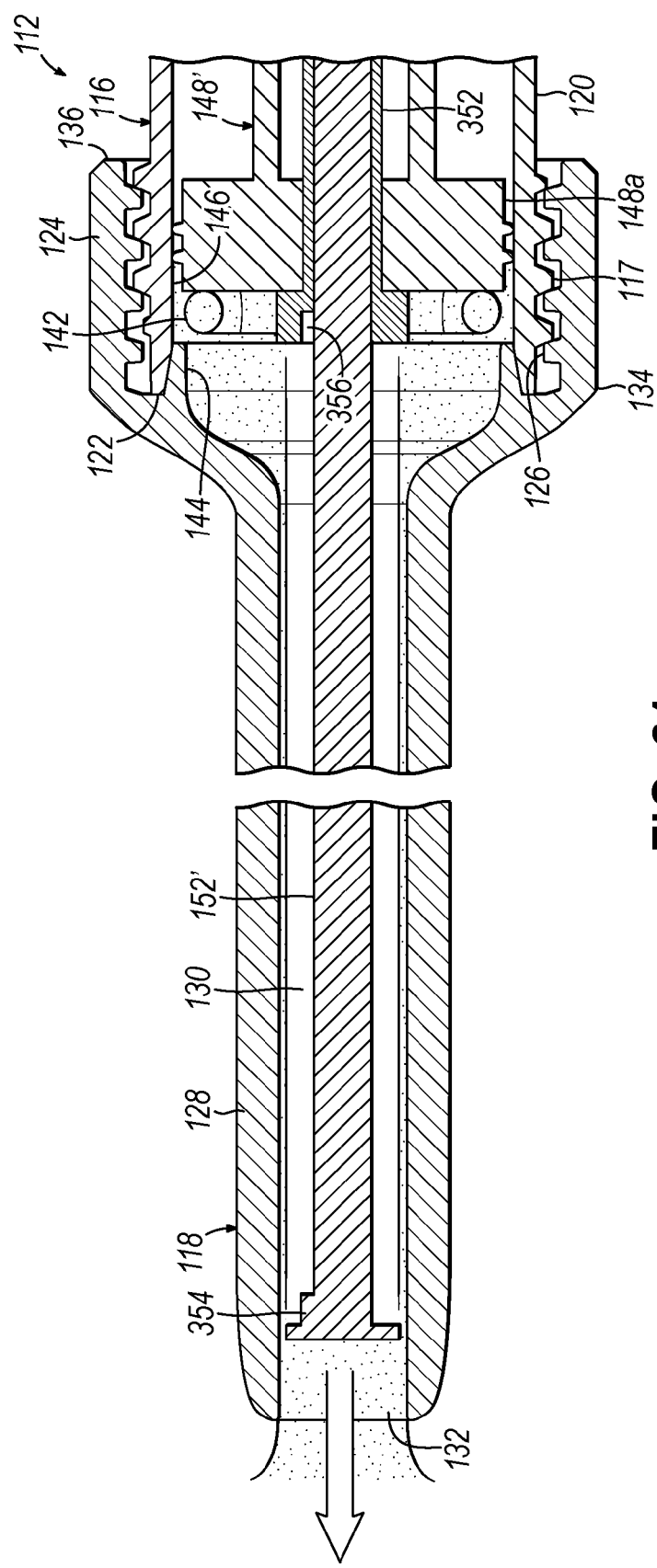
FIG. 21 is an enlarged cross sectional view illustrating further extrusion of material once the rod of the mixer is disconnected from the mixing element.

After the mixing operation is performed generally as previously described and as illustrated in FIG. 20, the proximally located connector assembly 350 is actuated to release the mixing rod 152' from its connection to the hollow shaft 352. As shown in FIGS. 20A and 20B, the connector assembly 350 includes a first connecting element 360 and a second connecting element 362. The first connecting element 360 is movable in a direction proximally along the second connecting element 362 and includes slots 364 for providing flexibility. The second connecting element 362 has a distal end 366 rigidly secured to the hollow shaft 352. More specifically, the distal end 366 of the second connecting element 362 may be epoxied or otherwise rigidly adhered to the proximal end of the hollow shaft 352, while the proximal end 368 of the second connecting element 362 includes one or more projections 370 that are selectively retained within an annular groove 372 of the mixer rod 152'. When the mixing operation is complete and the plunger element 148a and mixing element 142 have been pushed together to the bottom or distal end of the syringe barrel 116, the user then pulls back or proximally on the first connecting element 360 to release the mixer rod 152'. As the connecting element 360 is pulled proximally relative to the mixer rod 152', as shown in FIGS. 20A and 20B, a detent 378 moves from a first annular groove or recess 380 to a second, more proximally located annular groove or recess 382. This then prevents a proximal portion 384 of the first connecting element 360 from retaining the snap connection ends or projections 370 within the annular groove 372 and the mixer rod 152' may be pushed distally as illustrated in FIG. 20B while the first connecting element 360 is pulled proximally. This causes the snap projections 370 to be forced out of the annular groove 372 due to respectively chamfered surfaces 386, 388 of the projections 370 and groove 372 and due to the fact that the inner wall 390 of the first connecting element 360 is no longer holding the projections 370 within the annular groove 372. When the connector assembly 350 is in the position shown in FIG. 20B, the mixer rod 152' is then free to disengage in a linear fashion from the keys 354 and key way 356 connection at the distal end. As shown in FIG. 21, the mixer rod 152' may then be used to further extrude or push material out of the tip 118 generally as previously described.

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. A dispensing assembly, comprising:
   a syringe body comprising a barrel and a dispensing tip; and
   a mixing and plunging assembly configured to be removably coupled to the syringe body, the mixing and plunging assembly comprising a mixer and a plunger, the mixer being configured to mix material in the barrel, the mixer comprising a rod and a mixing element, the rod comprising a protrusion and the mixing element defining a groove configured to receive the protrusion of the rod, the mixing element being removably attached to the rod via a snap-fit attachment,
   at least one of the mixing element and the rod defining a groove to prevent the material from the barrel from being trapped between the mixing element and the rod,
   the plunger being configured to be depressed relative to the barrel to dispense material from the barrel through the dispensing tip, and the rod being configured to be detached from the mixing element and be used to push remaining material from the barrel through the dispensing tip.

2. The dispensing assembly of claim 1, wherein the rod includes a distal end, and the mixing element is removably attached to the distal end of the rod.

3. The dispensing assembly of claim 1, wherein the rod and plunger are configured to selectively limit slidable movement of the rod with respect to the plunger.

4. The dispensing assembly of claim 3, wherein the rod includes a first connecting portion and the plunger includes a second connecting portion and the first and second connecting portions are engageable and disengageable to allow the rod and the plunger to be connected and disconnected.

5. The dispensing assembly of claim 4, wherein the first connecting portion includes a protrusion and the second connecting portion includes a groove configured to receive the protrusion to form a snap-fit attachment between the rod and the plunger.

6. The dispensing assembly of claim 4, wherein the first connecting portion includes a first threaded portion and the second connecting portion includes a second threaded portion.

7. The dispensing assembly of claim 1, wherein the rod further includes a protrusion and the mixing element includes a groove configured to receive the protrusion to create a snap-fit attachment between the rod and the mixing element.

8. The dispensing assembly of claim 1, wherein the rod includes an auger tip configured to engage material in the syringe body.

9. The dispensing assembly of claim 1, wherein the mixing element includes a cutting surface configured to engage material in the syringe body.

10. The dispensing assembly of claim 1, wherein the mixing element has a shape that is generally complimentary with the shape of an interior of the syringe body near the dispensing tip.

11. The dispensing assembly of claim 1, wherein:
the rod includes a portion located outside of the syringe body when the mixer is coupled to the syringe body with the mixing element positioned within the syringe barrel, and
the dispensing assembly further comprises a connector assembly located outside of the syringe body and configured to be selectively actuated to attach and detach the rod and the mixing element.

12. The dispensing assembly of claim 11, wherein the mixer further comprises a hollow shaft receiving the rod, the hollow shaft having a proximal end and a distal end, wherein the mixing element is rigidly coupled to the distal end of the hollow shaft and a portion of the connector assembly is coupled to the proximal end of the hollow shaft.

13. The dispensing assembly of claim 12, wherein the connector assembly comprises a first connecting element and a second connecting element, wherein the first and second connecting elements are movable relative to each other between first and second positions, wherein the rod is configured to rotate and translate the mixing element when the first and second connecting elements are in the first position, and the rod is configured to translate relative to the mixing element to thereby push the remaining material through the dispensing tip when the first and second connecting elements are in the second position.

14. A method of dispensing material using a dispensing assembly having a syringe body and a mixing and plunging assembly, the method comprising:

moving a plunger of the mixing and plunging assembly relative to the syringe body to advance material from a barrel of the syringe body through a dispensing tip of the syringe body;
detaching a mixing element from a rod of the mixing and plunging assembly attached via a snap-fit attachment by pulling a protrusion of the rod out of a groove defined by the mixing element, wherein at least one of the mixing element and the rod defines a groove to prevent the material from the barrel from being trapped between the mixing element and the rod;
detaching the rod from the plunger of the mixing and plunging assembly; and
moving the rod into the dispensing tip to advance remaining material in the dispensing tip through the dispensing tip.

15. The method of claim 14, wherein detaching the mixing element includes actuating a connecting element located outside of the barrel.

16. The dispensing assembly of claim 1, wherein the plunger defines a passageway and the rod is received in the passageway.

17. The dispensing assembly of claim 16, wherein the plunger and the rod are configured to selectively limit slidable movement of the rod with respect to the plunger.

18. The dispensing assembly of claim 1, wherein the plunger and rod are configured to be removably attached with each other, and the rod is configured to be detached from the plunger before the rod is pushed into the dispensing tip.

19. A dispensing assembly, comprising:
a syringe body comprising a barrel and a dispensing tip; and
a mixing and plunging assembly configured to be removably coupled to the syringe body, the mixing and plunging assembly comprising a mixer and a plunger,
the mixer being configured to mix material in the barrel, the mixer comprising a rod and a mixing element removably attached to the rod,
the plunger being configured to be depressed relative to the barrel to dispense material from the barrel through the dispensing tip,
the rod being configured to be detached from the mixing element and be used to push remaining material from the barrel through the dispensing tip, and
the rod comprising an auger tip configured to engage the material in the barrel.

20. A dispensing assembly, comprising:
a syringe body comprising a barrel and a dispensing tip; and
a mixing and plunging assembly configured to be removably coupled to the syringe body, the mixing and plunging assembly comprising a mixer and a plunger,
the mixer being configured to mix material in the barrel, the mixer comprising a rod and a mixing element removably attached to the rod,
the plunger being configured to be depressed relative to the barrel to dispense material from the barrel through the dispensing tip,
the rod being configured to be detached from the mixing element and be used to push remaining material from the barrel through the dispensing tip, and
the mixing element comprising a cutting surface configured to engage material in the barrel.

21. A dispensing assembly, comprising:
a syringe body comprising a barrel and a dispensing tip;
a mixing and plunging assembly configured to be removably coupled to the syringe body, the mixing and plunging assembly comprising a mixer and a plunger, the mixer comprising a rod and a mixing element removably attached to the rod; and
a connector assembly located outside of the syringe body and configured to be selectively actuated to attach and detach the rod and the mixing element,
the mixer being configured to mix material in the barrel,
the plunger being configured to be depressed relative to the barrel to dispense the material from the barrel through the dispensing tip,
the rod being configured to be detached from the mixing element and be used to push remaining material from the barrel through the dispensing tip, and
the connector assembly comprising a first connecting element and a second connecting element, the first and second connecting elements being movable relative to each other between first and second positions, the rod configured to rotate and translate the mixing element when the first and second connecting elements are in the first position, and to translate relative to the mixing element to thereby push the remaining material through the dispensing tip when the first and second connecting elements are in the second position.

* * * * *